US008658387B2

(12) United States Patent  
Krah, III et al.

(10) Patent No.: US 8,658,387 B2  
(45) Date of Patent: *Feb. 25, 2014

(54) *EHRLICHIA CANIS* DIVA (DIFFERENTIATE INFECTED FROM VACCINATED ANIMALS)

(75) Inventors: Eugene Regis Krah, III, Freeport, ME (US); Melissa Beall, Cape Elizabeth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/956,390

(22) Filed: Nov. 30, 2010

(65) Prior Publication Data

US 2011/0091995 A1 Apr. 21, 2011

Related U.S. Application Data

(62) Division of application No. 11/397,222, filed on Apr. 4, 2006, now Pat. No. 7,842,473.

(60) Provisional application No. 60/668,205, filed on Apr. 4, 2005.

(51) Int. Cl.
*G01N 33/569* (2006.01)

(52) U.S. Cl.
USPC ........................................ 435/7.32

(58) Field of Classification Search
None
See application file for complete search history.

(56) References Cited

U.S. PATENT DOCUMENTS

| | | | |
|---|---|---|---|
| 4,894,576 A | 1/1990 | Okamoto et al. |
| 5,726,010 A | 3/1998 | Clark |
| 6,043,085 A | 3/2000 | Yu et al. |
| 6,355,777 B1 | 3/2002 | Walker et al. |
| 6,392,023 B1 | 5/2002 | Walker et al. |
| 6,403,780 B1 | 6/2002 | Walker et al. |
| 6,458,942 B1 | 10/2002 | Walker et al. |
| 6,660,269 B2 | 12/2003 | Walker et al. |
| 2002/0115840 A1 | 8/2002 | Walker et al. |
| 2003/0073095 A1 | 4/2003 | Walker et al. |
| 2003/0092087 A1 | 5/2003 | Walker et al. |
| 2003/0096250 A1 | 5/2003 | Walker et al. |
| 2003/0185849 A1 | 10/2003 | Walker et al. |
| 2004/0121433 A1 | 6/2004 | McBride et al. |
| 2004/0170972 A1 | 9/2004 | Chang |
| 2004/0198951 A1 | 10/2004 | Walker et al. |
| 2004/0247616 A1 | 12/2004 | Walker et al. |
| 2005/0260621 A1 | 11/2005 | McBride et al. |
| 2006/0211062 A1 | 9/2006 | O'Connor, Jr. |
| 2006/0234322 A1 | 10/2006 | Krah |
| 2007/0003570 A1 | 1/2007 | Murtaugh et al. |
| 2009/0004217 A1 | 1/2009 | Krah |
| 2009/0110691 A1 | 4/2009 | Krah et al. |

FOREIGN PATENT DOCUMENTS

| | | |
|---|---|---|
| WO | 98/42743 | 10/1998 |
| WO | 00/12688 | 3/2000 |
| WO | 01/82862 | 11/2001 |
| WO | 03/089571 | 10/2003 |
| WO | 2004/042037 | 5/2004 |
| WO | 2006/107924 | 10/2006 |
| WO | 2006/138509 | 12/2006 |
| WO | 2008/112007 | 9/2008 |

OTHER PUBLICATIONS

Breitschwerdt et al., "Doxycycline Hyclate Treatment of Experimental Canine Ehrlichiosis Followed by Challenge Inoculation with Two *Ehrlichia canis* Strains", Antimicrobial Agents and Chemotherapy, vol. 42, No. 2, p. 362-368, 1998.

Yu et al., "Comparison of *Ehrlichia chaffeensis* Recombinant Proteins for Serologic Diagnosis of Human Monocytotropic Ehrlichiosis", Journal of Clinical Microbiology, Vo. 37, No. 8, p. 2568-2575, 1999.

Yu et al., "Molecular Cloning and characterization of the 120-Kilodalton Protein Gene of *Ehrlichia canis* and application of the recombinant 120-Kilodalton protein for serodagnosis of canine Ehrlichiosis", Journal of Clinical Microbiology, vol. 38, No. 1, p. 369-374, 2000.

McBride et al., "Immunodiagnosis of *Ehrlichia canis* infection with recombinant proteins", Journal of Clinical Microbiology, vol. 39, No. 1, p. 315-322, 2001.

Accession No. NZ_AAEJ01000001 dated Oct. 4, 2004 (first page only).

Accession No. ZP_00211244 dated Oct. 4, 2004.
Accession No. ZP_00211130 dated Oct. 4, 2004.
Accession No. AAE96254 dated Apr. 20, 2002.
Accession No. ZP_00210575 dated Oct. 4, 2004.
Accession No. AAK01145 dated Oct. 6, 2003.
Accession No. AF252298 dated Oct. 6, 2003.
Accession No. AAD34330 dated Jan. 13, 2000.
Accession No. AF112369 dated Jan. 13, 2000.
Accession No. ZP_00211146 dated Oct. 4, 2004.

International Search Report and Written Opinion dated Feb. 2, 2007, for corresponding PCT application No. PCT/US2006/012432

International Search Report for corresponding PCT application No. PCT/US2007/080373 dated May 14, 2008.

Cardenas et al., "Enzyme-linked immunosorbent assay with conserved immunoreactive glycoproteins gp36 and gp19 has enhanced sensitivity and provides species-specific immunodiagnosis of *Ehrlichia canis* infection", Clinical and Vaccine Immunology, vol. 14, No. 2, p. 123-128, 2007.

McBride et al., "Kinetics of Antibody Response to *Ehrlichia canis* Immunoreactive Proteins", Infection and Immunity, vol. 71, No. 5, p. 2516-2524, 2003.

McBride et al., "Novel Immunoreactive glycoprotein orthologs of *Ehrlichia* spp.", Ann. NY Aca. Sci. 990:678-84, 2003—Abstract Only.

Office action dated Jan. 21, 2010, for U.S. Appl. No. 11/542,878 (US-2009-0004217).

(Continued)

*Primary Examiner* — Brain J Gangle

(74) *Attorney, Agent, or Firm* — McDonnell Boehnen Hulbert & Berghoff LLP

(57) ABSTRACT

*Ehrlichia canis* antigens that can be used to differentiate *E. canis* infected animals from animals that have been challenged with *E. canis*, e.g., vaccinated against *E. canis*, are disclosed. The invention also provides compositions and methods for determining the presence of *E. canis* antigens and antibodies.

18 Claims, 9 Drawing Sheets

(56) References Cited

OTHER PUBLICATIONS

Database, "Major outer membrane protein p19", Uniprot, Sep. 27, 2005. Retrieved from EBI Accession No. UNIPRO:Q3YSZ1, Database accession No. Q3YSZ1.

Mavromatis et al., "The genome of the obligately intracellular bacterium *Ehrlichia canis* reveals themes of complex membrane structure and immune evasion strategies", J. Bacteriol. 2006; 88(11):4015-23.

McBride et al., "Identification of a glycosylated *Ehrlichia canis* 19-kilodalton major immunoreactive protein with a species-specific serine-rich glycopeptide epitope", Infect. Immno. 2007; 75(1):74-82.

McBride et al., "Molecular cloning of the gene for a conserved major immunoreactive 28-kilodalton protein of *Ehrlichia canis*: a potential serodiagnostic antigen", Clin. Diagn. Lab. Immunol. 1999, 6(3):392-9.

Ndip et al., "Ehrlichial Infection in Cameroonian canines by *Ehrlichia canis* and *Ehrlichia ewingii*", Vet. Microbiol. 2005; 111(1-2):59-66.

Office Action issued in corresponding U.S. Appl. No. 11/542,878 (U.S. Publication No. 2009-0004217, published Jan. 1, 2099), dated Jun. 2, 2009.

Gauither et al., "Western immunoblot analysis for distinguishing vaccination and infection status with *Borrelia burgdorferi* (Lyme disease) in dogs", J. Vet. Diagn. Invest., 11:259-265 (1999).

Greenspan et al., "Defining epitopes: It's not as easy as it seems", Nature Biotechnology, vol. 17, pp. 936-937 (1999).

Homes, "PSMA specific antibodies and their diagnostic and therapeutic use", Exp. Opin. Invest. Drugs, 10(3), pp. 511-519 (2001).

Houghten et al., "Relative Importance of Position and Individual Amino Acid Residues in Peptide Antigen-Antibody Interactions: Implications in the Mechanism of Antigenic Drift and Antigenic Shift", Vaccines 86, eds. Brown et al., Cold Spring Harbor Laboratory Press, pp. 21-25 (1986).

Office action dated Apr. 1, 2010, for corresponding U.S. Appl. No. 12/262,709.

Waner et al., "Significance of serological testing for ehrlichial diseases in dogs with special emphasis on the diagnosis of canine monocytic ehrlichiosis caused by *Ehrlichia canis*", Veterinary Parasitology 95 (2001) 1-15.

International Search Report for corresponding PCT Application No. WO 2009/059170 dated May 7, 2009.

Western Analysis with Vaccinated Sera
Pool of 4 Vaccinated Dogs – 1:100

Figure 8
SEQ ID NO:15

MDIDNNNVTTSSTQDKSGNLMEVIMRILNFGNNSD
EKVSNEDTKVLVESLQPAVNDNVGNPSSEVGKEEN
APEVKAEDLQPAVDGSVEHSSSEVGKKVSETSKEE
STPEVKAEDLQPAVDGSIEHSSSEVGEKVSKTSKE
ESTPEVKAEDLQPAVDDSVEHSSSEVGEKVSETSK
EENTPEVKAEDLQPAVDGSIEHSSSEVGEKVSKTS
KEESTPEVKAEDLQPAVDDSVEHSSSEVGEKVSET
SKEENTPEVKAEDLQPAVDGSVEHSSSEVGEKVSK
TSKEESTPEVKAEDLQPAVDDSVEHSSSEVGEKVS
ETSKEENTPEVRAEDLQPAVDGSVEHSSSEVGEKV
SETSKEESTPEVKAEDLQPAVDSSIEHSSSEVGKK
VSETSKEESTPEVKAEDLQPAVDGSVEHSSSEVGE
KVSETSKEENTPEVKAEDLQPAVDGSVEHSSSEVG
EKVSETSKEENTPEVKAEDLQPAVDGSVEHSSSEV
GEKVSETSKEESTPEVKAEDLQPAVDDSVEHSSSE
VGEKVSETSKEESTPEVKAEDLQPAVDGSVEHSSS
EVGEKVSETSKEESTPEVKAEVQPVADGNPVPLNP
MPSIDNIDTNIIFHYHKDCKKGSAVGTDEMCCPVS
ELMAGEHVHMYGIYVYRVQSVKDLSGVFNIDHSTC
DCNLDVYFVGYNSFTNKETVDLI

```
KEENAPEVKAEDLQPAVDGSVEHSSSEVGKKVSETS
KEESTPEVKAEDLQPAVDGSIEHSSSEVGEKVSKTS
KEESTPEVKAEDLQPAVDDSVEHSSSEVGEKVSETS
KEENTPEVKAEDLQPAVDGSIEHSSSEVGEKVSKTS
KEESTPEVKAEDLQPAVDDSVEHSSSEVGEKVSETS
KEENTPEVKAEDLQPAVDGSVEHSSSEVGEKVSKTS
KEESTPEVKAEDLQPAVDDSVEHSSSEVGEKVSETS
KEENTPEVRAEDLQPAVDGSVEHSSSEVGEKVSETS
KEESTPEVKAEDLQPAVDSSIEHSSSEVGKKVSETS
KEESTPEVKAEDLQPAVDGSVEHSSSEVGEKVSETS
KEENTPEVKAEDLQPAVDGSVEHSSSEVGEKVSETS
KEENTPEVKAEDLQPAVDGSVEHSSSEVGEKVSETS
KEESTPEVKAEDLQPAVDDSVEHSSSEVGEKVSETS
KEESTPEVKAEDLQPAVDGSVEHSSSEVGEKVSETS
KEESTPEVKAE   SEQ ID NO:16
```

Figure 9A

```
KEESTPEVKAEDLQPAVDGSVEHSSSEVGEKVSETS    Consensus
   N    R       D I          K    K     SEQ ID NO:17
                S
```

Figure 9B

SEQUENCE LISTING

<160> NUMBER OF SEQ ID NOS: 17

<210> SEQ ID NO 1
<211> LENGTH: 2067
<212> TYPE: DNA
<213> ORGANISM: Ehrlichia canis

<400> SEQUENCE: 1
atggatattg ataacaataa tgtgactaca tcaagtacgc aagataaaag tgggaattta 60
atggaagtga ttatgcgtat attaaatttt ggtaataatt cagatgagaa agtaagcaat 120
gaagacacta aagttcttgt agagagttta caacctgctg tgaatgacaa tgtaggaaat 180
ccatcaagtg aagttggtaa agaagaaaat gctcctgaag ttaaagcgga agatttgcaa 240
cctgctgtag atggtagtgt agaacattca tcaagtgaag ttgggaaaaa agtatctgaa 300
actagtaaag aggaaagtac tcctgaagtt aaagcagaag atttgcaacc tgctgtagat 360
ggtagtatag aacattcatc aagtgaagtt ggagaaaaag tatctaaaac tagtaaagag 420
gaaagtactc ctgaagttaa agcagaagat ttgcaacctg ctgtagatga tagtgtggaa 480
cattcatcaa gtgaagttgg agaaaaagta tctgaaacta gtaaagagga aaatactcct 540
gaagttaaag cagaagattt gcaacctgct gtagatggta gtatagaaca ttcatcaagt 600
gaagttggag aaaaagtatc taaaactagt aaagaggaaa gtactcctga agttaaagca 660
gaagatttgc aacctgctgt agatgatagt gtggaacatt catcaagtga agttggagaa 720
aaagtatctg aaactagtaa agaggaaaat actcctgaag ttaaagcaga agatttgcaa 780
cctgctgtag atggtagtgt ggaacattca tcaagtgaag ttggagaaaa agtatctaaa 840
actagtaaag aggaaagtac tcctgaagtt aaagcagaag atttgcaacc tgctgtagat 900
gatagtgtgg aacattcatc aagtgaagtt ggagaaaaag tatctgaaac tagtaaagag 960
gaaaatactc ctgaagttag agcagaagat ttgcaacctg ctgtagatgg tagtgtagaa 1020
cattcatcaa gtgaagttgg agaaaaagta tctgaaacta gtaaagagga aagtactcct 1080
gaagttaaag cagaagattt gcaacctgct gtagatagta gtatagaaca ttcatcaagt 1140
gaagttggga aaaaagtatc tgaaactagt aaagaggaaa gtactcctga agttaaagca 1200
gaagatttgc aacctgctgt agatggtagt gtagaacatt catcaagtga agttggagaa 1260

```
aaagtatctg aaactagtaa agaggaaaat actcctgaag ttaaagcaga agatttgcaa    1320
cctgctgtag atggtagtgt agaacattca tcaagtgaag ttggagaaaa agtatctgaa    1380
actagtaaag aggaaaatac tcctgaagtt aaagcggaag atttgcaacc tgctgtagat    1440
ggtagtgtag aacattcatc aagtgaagtt ggagaaaaag tatctgaaac tagtaaagaa    1500
gaaagtactc ctgaagttaa agcagaagat ttgcaacctg ctgtagatga tagtgtagaa    1560
cattcatcaa gtgaagttgg agaaaaagta tctgaaacta gtaaagaaga aagtactcct    1620
gaagttaaag cggaagattt gcaacctgct gtagatggta gtgtggaaca ttcatcaagt    1680
gaagttggag aaaaagtatc tgagactagt aaagaggaaa gtactcctga agttaaagcg    1740
gaagtacagc ctgttgcaga tggtaatcct gttcctttaa atcctatgcc ttcaattgat    1800
aatattgata ctaatataat attccattac cataaagact gtaaaaaagg ttcagctgta    1860
ggaacagatg aaatgtgttg tcctgtatca gaattaatgg ctggggaaca tgttcatatg    1920
tatgaatttt atgtctatag agttcaatca gtaaggatt taagtggtgt atttaatata    1980
gatcattcta catgtgattg taatttagat gtttatttg taggatacaa ttctttact    2040 aacaaagaaa cagttgattt aatataa                                       2067
```

<210> SEQ ID NO 2
<211> LENGTH: 688
<212> TYPE: PRT
<213> ORGANISM: Ehrlichia canis

<400> SEQUENCE: 2

```
Met Asp Ile Asp Asn Asn Val Thr Thr Ser Ser Thr Gln Asp Lys
1               5                   10                  15

Ser Gly Asn Leu Met Glu Val Ile Met Arg Ile Leu Asn Phe Gly Asn
                20                  25                  30

Asn Ser Asp Glu Lys Val Ser Asn Glu Asp Thr Lys Val Leu Val Glu
            35                  40                  45

Ser Leu Gln Pro Ala Val Asn Asp Asn Val Gly Asn Pro Ser Ser Glu
        50                  55                  60

Val Gly Lys Glu Glu Asn Ala Pro Glu Val Lys Ala Glu Asp Leu Gln
65                  70                  75                  80

Pro Ala Val Asp Gly Ser Val Glu His Ser Ser Val Gly Lys
                    85                  90                  95

Lys Val Ser Glu Thr Ser Lys Glu Glu Ser Thr Pro Glu Val Lys Ala
                100                 105                 110

Glu Asp Leu Gln Pro Ala Val Asp Gly Ser Ile Glu His Ser Ser Ser
            115                 120                 125

Glu Val Gly Glu Lys Val Ser Lys Thr Ser Lys Glu Glu Ser Thr Pro
        130                 135                 140

Glu Val Lys Ala Glu Asp Leu Gln Pro Ala Val Asp Asp Ser Val Glu
145                 150                 155                 160

His Ser Ser Ser Glu Val Gly Glu Lys Val Ser Glu Thr Ser Lys Glu
                    165                 170                 175

Glu Asn Thr Pro Glu Val Lys Ala Glu Asp Leu Gln Pro Ala Val Asp
                180                 185                 190

Gly Ser Ile Glu His Ser Ser Glu Val Gly Glu Lys Val Ser Lys
            195                 200                 205

Thr Ser Lys Glu Glu Ser Thr Pro Glu Val Lys Ala Glu Asp Leu Gln
        210                 215                 220

Pro Ala Val Asp Asp Ser Val Glu His Ser Ser Ser Glu Val Gly Glu
```

```
                225                 230                 235                 240
Lys Val Ser Glu Thr Ser Lys Glu Glu Asn Thr Pro Glu Val Lys Ala
                245                 250                 255

Glu Asp Leu Gln Pro Ala Val Asp Gly Ser Val Glu His Ser Ser Ser
                260                 265                 270

Glu Val Gly Glu Lys Val Ser Lys Thr Ser Lys Glu Glu Ser Thr Pro
                275                 280                 285

Glu Val Lys Ala Glu Asp Leu Gln Pro Ala Val Asp Asp Ser Val Glu
                290                 295                 300

His Ser Ser Ser Glu Val Gly Glu Lys Val Ser Glu Thr Ser Lys Glu
305                 310                 315                 320

Glu Asn Thr Pro Glu Val Arg Ala Glu Asp Leu Gln Pro Ala Val Asp
                325                 330                 335

Gly Ser Val Glu His Ser Ser Glu Val Gly Lys Val Ser Glu
                340                 345                 350

Thr Ser Lys Glu Glu Ser Thr Pro Glu Val Lys Ala Glu Asp Leu Gln
                355                 360                 365

Pro Ala Val Asp Ser Ser Ile Glu His Ser Ser Glu Val Gly Lys
                370                 375                 380

Lys Val Ser Glu Thr Ser Lys Glu Glu Ser Thr Pro Glu Val Lys Ala
385                 390                 395                 400

Glu Asp Leu Gln Pro Ala Val Asp Gly Ser Val Glu His Ser Ser Ser
                405                 410                 415

Glu Val Gly Glu Lys Val Ser Glu Thr Ser Lys Glu Glu Asn Thr Pro
                420                 425                 430

Glu Val Lys Ala Glu Asp Leu Gln Pro Ala Val Asp Gly Ser Val Glu
                435                 440                 445

His Ser Ser Glu Val Gly Glu Lys Val Ser Glu Thr Ser Lys Glu
                450                 455                 460

Glu Asn Thr Pro Glu Val Lys Ala Glu Asp Leu Gln Pro Ala Val Asp
465                 470                 475                 480

Gly Ser Val Glu His Ser Ser Glu Val Gly Glu Lys Val Ser Glu
                485                 490                 495

Thr Ser Lys Glu Glu Ser Thr Pro Glu Val Lys Ala Glu Asp Leu Gln
                500                 505                 510

Pro Ala Val Asp Asp Ser Val Glu His Ser Ser Ser Glu Val Gly Glu
                515                 520                 525

Lys Val Ser Glu Thr Ser Lys Glu Glu Ser Thr Pro Glu Val Lys Ala
                530                 535                 540

Glu Asp Leu Gln Pro Ala Val Asp Gly Ser Val Glu His Ser Ser Ser
545                 550                 555                 560

Glu Val Gly Glu Lys Val Ser Glu Thr Ser Lys Glu Glu Ser Thr Pro
                565                 570                 575

Glu Val Lys Ala Glu Val Gln Pro Val Ala Asp Gly Asn Pro Val Pro
                580                 585                 590

Leu Asn Pro Met Pro Ser Ile Asp Asn Ile Asp Thr Asn Ile Ile Phe
                595                 600                 605

His Tyr His Lys Asp Cys Lys Lys Gly Ser Ala Val Gly Thr Asp Glu
                610                 615                 620

Met Cys Cys Pro Val Ser Glu Leu Met Ala Gly Glu His Val His Met
625                 630                 635                 640

Tyr Gly Ile Tyr Val Tyr Arg Val Gln Ser Val Lys Asp Leu Ser Gly
                645                 650                 655
```

-continued

```
Val Phe Asn Ile Asp His Ser Thr Cys Asp Cys Asn Leu Asp Val Tyr
            660                 665                 670

Phe Val Gly Tyr Asn Ser Phe Thr Asn Lys Glu Thr Val Asp Leu Ile
        675                 680                 685

<210> SEQ ID NO 3
<211> LENGTH: 3186
<212> TYPE: DNA
<213> ORGANISM: Ehrlichia canis

<400> SEQUENCE: 3
aatttagatt ttggacttgt agatggagat ggtaaaaatc ctttacatca tgctgttgaa     60
catttgccac ctgttatact taagggcgta atggaccatg taaaaaatag tagtgagttt    120
caagatttag taaatgatcc tgattatttt ggaaatacta tagctcatta tgcagttaag    180
aataaaaatg ctgatttaac attgtttaac atgctgaaag cttcaggagc tgatttaaat    240
gttaggaatg tagttggtcg agctccaata catgttgctt cttctaatgg taaggctaat    300
gcagtttctg gacttgtatc atgtggtatt gacgttaatt ctcaagatgt gaatggagat    360
acaccacttc atattgctgt tgaaggcggt agtatggaga cggtattagc agtgttaaat    420
cagagaggtg ctgatgttag tgtccagaat aacgatggag ttacacctat gcttagtgct    480
gctaaatatg gagatatagg tgtaataaaa gctttaggtt cagctaaacc aaatattaaa    540
ggtgaagaca ctgttgctaa atcattgctg atggaggatt acaaaggttt tacacccttg    600
cattttgtag ctggtggtgg tagcagagat acattccgtg tcgtaagaaa aaattatgaa    660
aaatgtcatg acttagctac tattagggca gctttaatgc aagatagaag tggtggtgag    720
cttgtaaatt taggggattt tgaaagtgaa aatatattgg gttcgccaaa tgcaaaattc    780
ttgcagcata ttcaatcagc aaattttggt tttctccag cgcattgtgc tatagtatcg     840
tctaatcaca atgtaatgaa agatatctta aattttgttg ggattcgtt acacctacca     900 agtgagcgtg ggtataatgc aatgcaggtt gctgctttgt ttggtgacaa agaagcagtg    960
aaaatgcttg ctaaaagtgc taagccaagt gatcttaatt ttaagacttc agcaactcct   1020
actccgttaa atcttgcatg tcttagaggt gataatgagg tagtacgtgg gttagtaggt   1080
caacatggta ttgacattaa ccaacgtatg ggaagtgata aaaacactgt attgcattat   1140
gcaatcagca aaggagatag ttttcttgtg caaaagatat tagctcatac tggagttgat   1200
gttaattgtg agaataacct aggtcaaacg cctttacatt tagcagttga gggaggagat   1260
cctaagatag tatcttctct tcttaaagct ggtgcagtag ttaatcgtct ggatgataat   1320
ggtagatctg tactttcttc tgcgatagtt ccaggtagaa aagaaaaggg agtgctgggt   1380
atagttaata aattgctgga tagaggtgca gatattaatt tagatggaga ccacaatata   1440
ctttttgatc agtgtctaag ggtggatat aataatgtat tagataagtt aatacaacaa    1500
ggggttgaag ttaatcgaaa tagtgaaata cgtccaatgg tttatgctgc aatatctggt   1560
aatgagcatg ctatcaaatc attagctaat gctggtggag atgttaatga agtagtaaat   1620
aatccatcta gtaggcattc aggaaatcct ttaattatgg ttgcagtagc agatggtaat   1680
gcaggtcttc ttaaaacatt agtttctgaa ggatgtgatg ttggtaaatc tggaaaagat   1740
ggtaatacag cgttacatta tgctgttagt cattcagata aagagtttgg taataaagct   1800
ataaagatat taatttcacg taatagtgtt gggactaata gagatattct tactcaaaag   1860
aataacgcag gtgatacacc tttacatgaa gctcttaagt caggtaatat taattctgta   1920
cagaatatct taagtgctgt acatccaaga tacgcaaagg agatattaac agccagagac   1980
```

-continued

```
aaagaagggt acacaccaat gcattatact gttggagtaa ataatgttga tgttggtaga    2040
agtattctag agtctatgct ctctaaaggt gtgaataatc ttggagagat tgttggagca    2100
caggatagta attttcgaac acctctgcat gctgctatta aatatctga ttatcgtgct     2160 gcggacatga taataggtag cttatcgaaa acagaattgt caaagttatc gcaattaaca    2220
gatattaacg gggatacacc actacatctt tcttgtcagt ctggtaatgt cgagatgaca    2280
caattctttc ttggaggttt ggataaacgt gaattaccta agacattaaa gatagcaaat    2340
aaaaatggag atactccttt acatgatgct ataagaaatg atgatattaa atctgcaaaa    2400
atgatgatta ggaattgtaa caaagaagaa cttgctaatg tattaaaatg taaagatagt    2460
tttggtaata cagtattgca tactattgct gaccaagtta ttgcgaatcc agaatcaaag    2520
aaagaccttg atggtttgat gaatttagca gtgaaaaggc taaagaatca agatctgaaa    2580
gatctagtta atacgcgaaa taactctgac gatactgttg cacattgtgc tcttttatcg    2640
gatatgaaat atgctcaaaa gatacttaaa tcatgtaacc atgatacatt agtgagagga    2700
aatagtaata atcaatcttt atcagagtgt attcgtgatg atagtaaata taaaaaaggt    2760
ggaattttta gtaagtcttt attttcaaaa ttaaagaaac ttgaggcacg agctgccagc    2820
gctagttatg aagaattatc tagtatcagt agtggtagtg atgtttcttc tgtatcaaca    2880
aatagcacag aagtaagtgc agtacctgaa gtggcaagaa gtagtggtgc tgtgtcgttc    2940
aaacatgtgc aagaaacagg agttgacacg tctggtcctt ctgatataga aagtttagag    3000
agattatctg atactagtct tgggtcaaat gattttgatc agcgaatggc agatttagat    3060
caagaaatag caaatattgt tagtggttta ccagaagtta cccaggtagc tgtaagtcaa    3120
caacaagcag catctcctag ttcaggtcaa gctgctggtg tgcaacaaaa agagatgcag    3180
agataa                                                               3186
```

<210> SEQ ID NO 4
<211> LENGTH: 1061
<212> TYPE: PRT
<213> ORGANISM: Ehrlichia canis

<400> SEQUENCE: 4

```
Asn Leu Asp Phe Gly Leu Val Asp Gly Asp Gly Lys Asn Pro Leu His
1               5                   10                  15

His Ala Val Glu His Leu Pro Pro Val Ile Leu Lys Gly Val Met Asp
            20                  25                  30

His Val Lys Asn Ser Ser Glu Phe Gln Asp Leu Val Asn Asp Pro Asp
        35                  40                  45

Tyr Phe Gly Asn Thr Ile Ala His Tyr Ala Val Lys Asn Lys Asn Ala
    50                  55                  60

Asp Leu Thr Leu Phe Asn Met Leu Lys Ala Ser Gly Ala Asp Leu Asn
65                  70                  75                  80

Val Arg Asn Val Val Gly Arg Ala Pro Ile His Val Ala Ser Ser Asn
                85                  90                  95

Gly Lys Ala Asn Ala Val Ser Gly Leu Val Ser Cys Gly Ile Asp Val
            100                 105                 110

Asn Ser Gln Asp Val Asn Gly Asp Thr Pro Leu His Ile Ala Val Glu
        115                 120                 125

Gly Gly Ser Met Glu Thr Val Leu Ala Val Leu Asn Gln Arg Gly Ala
    130                 135                 140

Asp Val Ser Val Gln Asn Asn Asp Gly Val Thr Pro Met Leu Ser Ala
145                 150                 155                 160
```

-continued

Ala Lys Tyr Gly Asp Ile Gly Val Ile Lys Ala Leu Gly Ser Ala Lys
                165                 170                 175

Pro Asn Ile Lys Gly Glu Asp Thr Val Ala Lys Ser Leu Leu Met Glu
            180                 185                 190

Asp Tyr Lys Gly Phe Thr Pro Leu His Phe Val Ala Gly Gly Gly Ser
        195                 200                 205

Arg Asp Thr Phe Arg Val Val Arg Lys Asn Tyr Glu Lys Cys His Asp
    210                 215                 220

Leu Ala Thr Ile Arg Ala Ala Leu Met Gln Asp Arg Ser Gly Gly Glu
225                 230                 235                 240

Leu Val Asn Leu Gly Asp Phe Glu Ser Glu Asn Ile Leu Gly Ser Pro
                245                 250                 255

Asn Ala Lys Phe Leu Gln His Ile Gln Ser Ala Asn Phe Gly Phe Ser
            260                 265                 270

Pro Ala His Cys Ala Ile Val Ser Ser Asn His Asn Val Met Lys Asp
        275                 280                 285

Ile Leu Asn Phe Val Gly Asp Ser Leu His Leu Pro Ser Glu Arg Gly
    290                 295                 300

Tyr Asn Ala Met Gln Val Ala Ala Leu Phe Gly Asp Lys Glu Ala Val
305                 310                 315                 320

Lys Met Leu Ala Lys Ser Ala Lys Pro Ser Asp Leu Asn Phe Lys Thr
                325                 330                 335

Ser Ala Thr Pro Thr Pro Leu Asn Leu Ala Cys Leu Arg Gly Asp Asn
            340                 345                 350

Glu Val Val Arg Gly Leu Val Gly Gln His Gly Ile Asp Ile Asn Gln
        355                 360                 365

Arg Met Gly Ser Asp Lys Asn Thr Val Leu His Tyr Ala Ile Ser Lys
    370                 375                 380

Gly Asp Ser Phe Leu Val Gln Lys Ile Leu Ala His Thr Gly Val Asp
385                 390                 395                 400

Val Asn Cys Glu Asn Asn Leu Gly Gln Thr Pro Leu His Leu Ala Val
                405                 410                 415

Glu Gly Gly Asp Pro Lys Ile Val Ser Ser Leu Leu Lys Ala Gly Ala
            420                 425                 430

Val Val Asn Arg Leu Asp Asp Asn Gly Arg Ser Val Leu Ser Ser Ala
        435                 440                 445

Ile Val Pro Gly Arg Lys Glu Lys Gly Val Leu Gly Ile Val Asn Lys
    450                 455                 460

Leu Leu Asp Arg Gly Ala Asp Ile Asn Leu Asp Gly Asp His Asn Ile
465                 470                 475                 480

Leu Phe Asp Gln Cys Leu Arg Gly Gly Tyr Asn Asn Val Leu Asp Lys
                485                 490                 495

Leu Ile Gln Gln Gly Val Glu Val Asn Arg Asn Ser Glu Ile Arg Pro
            500                 505                 510

Met Val Tyr Ala Ala Ile Ser Gly Asn Glu His Ala Ile Lys Ser Leu
        515                 520                 525

Ala Asn Ala Gly Gly Asp Val Asn Glu Val Val Asn Pro Ser Ser
    530                 535                 540

Arg His Ser Gly Asn Pro Leu Ile Met Val Ala Val Ala Asp Gly Asn
545                 550                 555                 560

Ala Gly Leu Leu Lys Thr Leu Val Ser Glu Gly Cys Asp Val Gly Lys
                565                 570                 575

Ser Gly Lys Asp Gly Asn Thr Ala Leu His Tyr Ala Val Ser His Ser
            580                 585                 590

```
Asp Lys Glu Phe Gly Asn Lys Ala Ile Lys Ile Leu Ile Ser Arg Asn
            595                 600                 605
Ser Val Gly Thr Asn Arg Asp Ile Leu Thr Gln Lys Asn Asn Ala Gly
        610                 615                 620
Asp Thr Pro Leu His Glu Ala Leu Lys Ser Gly Asn Ile Asn Ser Val
625                 630                 635                 640
Gln Asn Ile Leu Ser Ala Val His Pro Arg Tyr Ala Lys Glu Ile Leu
                645                 650                 655
Thr Ala Arg Asp Lys Glu Gly Tyr Thr Pro Met His Tyr Thr Val Gly
            660                 665                 670
Val Asn Asn Val Asp Val Gly Arg Ser Ile Leu Glu Ser Met Leu Ser
        675                 680                 685
Lys Gly Val Asn Leu Gly Glu Ile Val Gly Ala Gln Asp Ser Asn
        690                 695                 700
Phe Arg Thr Pro Leu His Ala Ala Ile Lys Ile Ser Asp Tyr Arg Ala
705                 710                 715                 720
Ala Asp Met Ile Ile Gly Ser Leu Ser Lys Thr Glu Leu Ser Lys Leu
                725                 730                 735
Ser Gln Leu Thr Asp Ile Asn Gly Asp Thr Pro Leu His Leu Ser Cys
            740                 745                 750
Gln Ser Gly Asn Val Glu Met Thr Gln Phe Phe Leu Gly Gly Leu Asp
        755                 760                 765
Lys Arg Glu Leu Pro Lys Thr Leu Lys Ile Ala Asn Lys Asn Gly Asp
        770                 775                 780
Thr Pro Leu His Asp Ala Ile Arg Asn Asp Ile Lys Ser Ala Lys
785                 790                 795                 800
Met Met Ile Arg Asn Cys Asn Lys Glu Leu Ala Asn Val Leu Lys
                805                 810                 815
Cys Lys Asp Ser Phe Gly Asn Thr Val Leu His Thr Ile Ala Asp Gln
            820                 825                 830
Val Ile Ala Asn Pro Glu Ser Lys Lys Asp Leu Asp Gly Leu Met Asn
        835                 840                 845
Leu Ala Val Lys Arg Leu Lys Asn Gln Asp Leu Lys Asp Leu Val Asn
        850                 855                 860
Thr Arg Asn Asn Ser Asp Asp Thr Val Ala His Cys Ala Leu Leu Ser
865                 870                 875                 880
Asp Met Lys Tyr Ala Gln Lys Ile Leu Lys Ser Cys Asn His Asp Thr
                885                 890                 895
Leu Val Arg Gly Asn Ser Asn Asn Gln Ser Leu Ser Glu Cys Ile Arg
            900                 905                 910
Asp Asp Ser Lys Tyr Lys Lys Gly Gly Ile Phe Ser Lys Ser Leu Phe
        915                 920                 925
Ser Lys Leu Lys Lys Leu Glu Ala Arg Ala Ala Ser Ala Ser Tyr Glu
        930                 935                 940
Glu Leu Ser Ser Ile Ser Ser Gly Ser Asp Val Ser Val Ser Thr
945                 950                 955                 960
Asn Ser Thr Glu Val Ser Ala Val Pro Glu Val Ala Arg Ser Ser Gly
                965                 970                 975
Ala Val Ser Phe Lys His Val Gln Glu Thr Gly Val Thr Ser Gly
            980                 985                 990
Pro Ser Asp Ile Glu Ser Leu Glu  Arg Leu Ser Asp Thr  Ser Leu Gly
        995                 1000                1005

Ser Asn  Asp Phe Asp Gln Arg  Met Ala Asp Leu Asp  Gln Glu Ile
```

```
            1010             1015             1020
Ala Asn  Ile Val Ser Gly Leu Pro Glu Val Thr Gln  Val Ala Val
        1025                1030                1035

Ser Gln  Gln Gln Ala Ala Ser Pro Ser Ser Gly Gln  Ala Ala Gly
        1040                1045                1050

Val Gln  Gln Lys Glu Met Gln Arg
        1055                1060

<210> SEQ ID NO 5
<211> LENGTH: 2373
<212> TYPE: DNA
<213> ORGANISM: Ehrlichia canis

<400> SEQUENCE: 5
aattatgctg aaactacttt atcatttggt gaatctcgag cagaaggacg tgaatctcca      60
tcaagtgcat ttgttcaaac tggtcaatca gaagtacctc ggagtgaggc tgcagagcca     120
ttaattcaat ttcctcatga tgaagaaagt actgcattag gttctcaagc aactatgaca     180
ggagtgtcta ctcaggctag tccgtcagca gcatatcagg atgatagtga aatatcacgt     240
atgaggtcta tggcaggaac atctgctcaa gctgatcaat cagcagtaca tcgtcggagt     300
ggtacagcat tagagccatt aattgaattg cctgatgaag aagaaaatgc tgcattagat     360
tttcaaacag ctatgacagg agtgcctact caggctagtc cgtcagcagt acatcggagt     420
ggtgttgcat cagatcctac gctacctgat gatgaaagaa ttgatgttcc atcagtttca     480
tctcaagttg taagaccttt tagtgatggt gaagattatt cagtatatga taaatcaggt     540
gtagtaagtg gtcatgaaag acctgttcct tctagagatt caagacaatt ggatgcattt     600
ggtgatccat cagatgattt attgccggag agtgaaatta ttgttagcag cagtaagaaa     660
gcaatattag atagccaaaa tgaaatagaa tctcttattc agagtggaga tacttctaga     720
tgtattaggg caattaatag tgctcctagt gcgtcagtgt ttcaactgaa gactttatcg     780
aatgatatat ctattgctgg acgtgctttt ttaaatggta atattgattt aatagaagct     840
tgtatgaatt ctggcaagaa attaaatcca aatattactg ataatgaaaa aaatactcta     900
ttacatcaat ttgtaggata ttttgaacgc gatccgagaa tgttgcttga tgcaggaatg     960
cgtaatctgt ttttgagatt atgcatggat tatggtttcg atattaatca taaaaatagt    1020
aatggtaata cagtacttga tagattaaat gatttagtag aagggttaag tagttcgcaa    1080
gttgatcttg aaagtagtgg tattgatgag tttatgatct cattgttagc tcattctaga    1140
atgagtgatc aagcagtaaa gaatattgct actgcgcaaa atgagttttt tgcacgtgat    1200 tctgttttata atattagtcg tttagttgat acttctatag ttttgcagaa taaattcagt    1260
gaagtatttt atgaagtctg tggacgtatt ttatctgaag aagctggtaa acataagggt    1320
gttgctgaag caaattattc aagattgaat aaaatattaa atgatgaatg tcttagaaag    1380
actttagcta atacagatgc cgatggaaat aatgttttac agagattgtg tcaagatatt    1440
gcttctggaa aaatcaatgc tcgtgatgac agagtattaa aacttttttga gacaattata    1500 tctaatttaa aagacaaaga taagcatta ctagaggatt tattattaa aatagaaac    1560 tcaagatttg aaaattgcat tgaagctata ccacgtattc ctggtgccga tgctctattt    1620
aaaaaactag aagagttatt attaaaaaag aaaatagcag agtcttgtga ttttaattct    1680
atgttagtga attgtgctga gtctgctaat gataatttat ataattaccct gcgcactaat    1740 tatgcagtta ttggtataaa taacgtagat ataaatggca attcatccct atgtaaagct    1800
gttgttactg ggtcacaagg tattgttaaa gcagtattat caactggaac taatattaat    1860
```

-continued

```
aggaaagata aaaatggtaa tacacccttta catgcattgt taattttat gatgtctaac    1920 cctgaacttg tcaaggagca acatatttca cttgtgaaat tcttagcgtc tcgtggagct    1980
ttacttaatg taaaaaataa tatgaatatt tctccaatta tgcttgcaga atctattgat    2040
aagaaagagg aacttgctaa gaaatttaca aatcaaaaag ttagtatttt agaatcttta    2100
atagctggta gtgaagaaca tttagggctt aaatccaaat gtatatctga gttaaagcct    2160
tatatagaat taggaaaagg catgaagtac gaagatatac atgctgatgt aataggtggt    2220
gtattatctg ctgatatgtg taatgctaga ttgcagatag gtaaattatt aaatggtgat    2280
ttttgtaaag aaaatgaatt aaagacagta aaatttaatt tttctgatac aaataagggt    2340
tatgtacaaa atgttggtaa aaaaagaaat tat                                 2373
```

<210> SEQ ID NO 6
<211> LENGTH: 791
<212> TYPE: PRT
<213> ORGANISM: Ehrlichia canis

<400> SEQUENCE: 6

```
Asn Tyr Ala Glu Thr Thr Leu Ser Phe Gly Glu Ser Arg Ala Glu Gly
 1               5                  10                  15

Arg Glu Ser Pro Ser Ser Ala Phe Val Gln Thr Gly Gln Ser Glu Val
            20                  25                  30

Pro Arg Ser Glu Ala Ala Glu Pro Leu Ile Gln Phe Pro His Asp Glu
        35                  40                  45

Glu Ser Thr Ala Leu Gly Ser Gln Ala Thr Met Thr Gly Val Ser Thr
    50                  55                  60

Gln Ala Ser Pro Ser Ala Ala Tyr Gln Asp Asp Ser Glu Ile Ser Arg
65                  70                  75                  80

Met Arg Ser Met Ala Gly Thr Ser Ala Gln Ala Asp Gln Ser Ala Val
                85                  90                  95

His Arg Arg Ser Gly Thr Ala Leu Glu Pro Leu Ile Glu Leu Pro Asp
           100                 105                 110

Glu Glu Glu Asn Ala Ala Leu Asp Phe Gln Thr Ala Met Thr Gly Val
       115                 120                 125

Pro Thr Gln Ala Ser Pro Ser Ala Val His Arg Ser Gly Val Ala Ser
   130                 135                 140

Asp Pro Thr Leu Pro Asp Asp Glu Arg Ile Asp Val Pro Ser Val Ser
145                 150                 155                 160

Ser Gln Val Val Arg Pro Phe Ser Asp Gly Asp Tyr Ser Val Tyr
               165                 170                 175

Asp Lys Ser Gly Val Val Ser Gly His Glu Arg Pro Val Ser Ser Arg
           180                 185                 190

Asp Ser Arg Gln Leu Asp Ala Phe Gly Asp Pro Ser Asp Leu Leu
       195                 200                 205

Pro Glu Ser Glu Ile Ile Val Ser Ser Ser Lys Lys Ala Ile Leu Asp
   210                 215                 220

Ser Gln Asn Glu Ile Glu Ser Leu Ile Gln Ser Gly Asp Thr Ser Arg
225                 230                 235                 240

Cys Ile Arg Ala Ile Asn Ser Ala Pro Ser Ala Ser Val Phe Gln Leu
               245                 250                 255

Lys Thr Leu Ser Asn Asp Ile Ser Ile Ala Gly Arg Ala Phe Leu Asn
           260                 265                 270

Gly Asn Ile Asp Leu Ile Glu Ala Cys Met Asn Ser Gly Lys Lys Leu
       275                 280                 285
```

-continued

Asn Pro Asn Ile Thr Asp Asn Glu Lys Asn Thr Leu His Gln Phe
    290                 295                 300

Val Gly Tyr Phe Glu Arg Asp Pro Arg Met Leu Leu Asp Ala Gly Met
305                 310                 315                 320

Arg Asn Leu Phe Leu Arg Leu Cys Met Asp Tyr Gly Phe Asp Ile Asn
                325                 330                 335

His Lys Asn Ser Asn Gly Asn Thr Val Leu Asp Arg Leu Asn Asp Leu
        340                 345                 350

Val Glu Gly Leu Ser Ser Ser Gln Val Asp Leu Glu Ser Ser Gly Ile
            355                 360                 365

Asp Glu Phe Met Ile Ser Leu Leu Ala His Ser Arg Met Ser Asp Gln
    370                 375                 380

Ala Val Lys Asn Ile Ala Thr Ala Gln Asn Glu Phe Phe Ala Arg Asp
385                 390                 395                 400

Ser Val Tyr Asn Ile Ser Arg Leu Val Asp Thr Ser Ile Val Leu Gln
                405                 410                 415

Asn Lys Phe Ser Glu Val Phe Tyr Glu Val Cys Gly Arg Ile Leu Ser
        420                 425                 430

Glu Glu Ala Gly Lys His Lys Gly Val Ala Glu Ala Asn Tyr Ser Arg
            435                 440                 445

Leu Asn Lys Ile Leu Asn Asp Glu Cys Leu Arg Lys Thr Leu Ala Asn
    450                 455                 460

Thr Asp Ala Asp Gly Asn Asn Val Leu Gln Arg Leu Cys Gln Asp Ile
465                 470                 475                 480

Ala Ser Gly Lys Ile Asn Ala Arg Asp Asp Arg Val Leu Lys Leu Phe
                485                 490                 495

Glu Thr Ile Ile Ser Asn Leu Lys Asp Lys Asp Lys Ala Leu Leu Glu
        500                 505                 510

Asp Leu Leu Phe Asn Asn Arg Asn Ser Arg Phe Glu Asn Cys Ile Glu
            515                 520                 525

Ala Ile Pro Arg Ile Pro Gly Ala Asp Ala Leu Phe Lys Lys Leu Glu
    530                 535                 540

Glu Leu Leu Leu Lys Lys Ile Ala Glu Ser Cys Asp Phe Asn Ser
545                 550                 555                 560

Met Leu Val Asn Cys Ala Glu Ser Ala Asn Asp Asn Leu Tyr Asn Tyr
                565                 570                 575

Leu Arg Thr Asn Tyr Ala Val Ile Gly Ile Asn Asn Val Asp Ile Asn
        580                 585                 590

Gly Asn Ser Ser Leu Cys Lys Ala Val Val Thr Gly Ser Gln Gly Ile
            595                 600                 605

Val Lys Ala Val Leu Ser Thr Gly Thr Asn Ile Asn Arg Lys Asp Lys
    610                 615                 620

Asn Gly Asn Thr Pro Leu His Ala Leu Leu Ile Phe Met Met Ser Asn
625                 630                 635                 640

Pro Glu Leu Val Lys Glu Gln His Ile Ser Leu Val Lys Phe Leu Ala
                645                 650                 655

Ser Arg Gly Ala Leu Leu Asn Val Lys Asn Asn Met Asn Ile Ser Pro
        660                 665                 670

Ile Met Leu Ala Glu Ser Ile Asp Lys Lys Glu Leu Ala Lys Lys
            675                 680                 685

Phe Thr Asn Gln Lys Val Ser Ile Leu Glu Ser Leu Ile Ala Gly Ser
    690                 695                 700

Glu Glu His Leu Gly Leu Lys Ser Lys Cys Ile Ser Glu Leu Lys Pro

|   |   |   | 705 |   |   |   | 710 |   |   |   | 715 |   |   |   | 720 |
|---|---|---|---|---|---|---|---|---|---|---|---|---|---|---|---|

Tyr Ile Glu Leu Gly Lys Gly Met Lys Tyr Glu Asp Ile His Ala Asp
                        725                                  730                                  735

Val Ile Gly Gly Val Leu Ser Ala Asp Met Cys Asn Ala Arg Leu Gln
                  740                                  745                                  750

Ile Gly Lys Leu Leu Asn Gly Asp Phe Cys Lys Glu Asn Glu Leu Lys
                  755                                  760                                  765

Thr Val Lys Phe Asn Phe Ser Asp Thr Asn Lys Gly Tyr Val Gln Asn
                  770                                  775                                  780

Val Gly Lys Lys Arg Asn Tyr
785                          790

<210> SEQ ID NO 7
<211> LENGTH: 2283
<212> TYPE: DNA
<213> ORGANISM: Ehrlichia canis

<400> SEQUENCE: 7

| | | | | | |
|---|---|---|---|---|---|
| gtaaaaaaat | taagattatt | attaaattca | ataagtgagt | taccgcaaga | attaaaagat | 60 |
| caaatttaa | gtactagaag | tactatagat | aaattacgaa | atagaattaa | tgcctgcata | 120 |
| aagtctgacg | atagagaagg | tattgcacat | gctgtagaat | ctatggctag | ttcttattgt | 180 |
| gaattattag | gacattgtag | attaattttt | aagaaattat | atgatgaaaa | tgctgataaa | 240 |
| agtttgctag | aattatgtat | taagaatat | caatctgatt | taaacaaatt | attggaacaa | 300 |
| ggtattgata | tatgtgcttc | agaagtctca | tcagaatgta | aggatttagt | ttgtaaagta | 360 |
| tgtgaagatg | aatttgagaa | atatgactct | ttatctaaag | tacaaagatt | cagggaatta | 420 |
| tctggtgaaa | ttgctgattt | ggatgataaa | ttaacaagaa | gggcttcttt | tgttgagact | 480 |
| tttggattat | ttagcagtag | attaagacat | tatagggaaa | ttttaggaga | tggtgattta | 540 |
| aaatttcgag | agaggatagt | tgaaaatat | caagaggatt | taaggaatt | attagaatta | 600 |
| tctgttgatc | ttcatttgtt | aataaattta | ccagcattag | aagatttacg | cgatcataga | 660 |
| aatttagtgc | atagagcatg | taatgctgaa | attgaaaaat | atctaacttt | atttgatgat | 720 |
| caacaattac | gtacattatc | gcaagaagtg | aataatgctc | atggtgaatt | gatacagatg | 780 |
| ttttctaagt | ttagtatatt | tgttgatggc | gttactggta | ttgaacagag | cacatctcaa | 840 |
| gtagagcacc | ctcgttctga | tattgctaaa | agagatacta | caacaccaaa | gcaacgtgtt | 900 |
| gtgcaaggta | aagatgatat | acaatctagt | gatagtgata | gtgatagtga | tagtaaatac | 960 |
| ggtgatgatg | atagtaaaaa | agcatcagtt | agtgcacctg | ctgttgacca | agttgtacct | 1020 |
| gtagctgatg | ttcaacctga | acctcagcta | ggtgaaggat | tggaaacatt | agagtctagt | 1080 |
| atagctgaag | gacctgagtt | gcctggtgat | gcatctactg | ctaagcaatc | tataccttt | 1140 |
| gcgataacac | catcaagtcc | tgagacagtt | gatgaaaaac | ttgaaagttc | tggtgttagt | 1200 |
| caagatggta | ttacaacacc | aggacaacgt | gttgtgcaag | gtaaagatga | tatacaatct | 1260 |
| agtgatagtg | atagtgatag | taaatacggt | gatgatgata | gtaaaaaagc | atcagctagt | 1320 |
| gcacctgctg | ttgaccaagt | tgtacctgta | gctgatgttc | aacctgaacc | tcagctaggt | 1380 |
| gaaaaattgg | aaacattaga | gtctagtata | actaaaggac | ctgagttgcc | tggtgatgca | 1440 |
| tctactgcta | agcaatctat | accttttgcg | ataacaccat | caagtcctga | gacagttgat | 1500 |
| gaaaaacttg | aaagttctgg | tgttagtcaa | gatggtatta | caacaccagg | acaacgtgtt | 1560 |
| gtgcaaggta | aagatgatat | acaatctagt | gatagtgata | gtgatagtaa | ataccggtgat | 1620 |
| gatgatagta | aaaaagcatc | agctagtgca | cctgctgttg | accaagttgt | accttctgac | 1680 |

```
actcgtgcag atggagtatc agaaccatta gcatctcatg tggatcaagg atctgatgta   1740
cctggtgatg catctgttga tggtgttgat ttaagattag gacggttatc tactgagcaa   1800
agtggattgt tgccacgtca tgaacaaaat gtaagagcat ttattttaga acagagtttg   1860
ttagatcaat tatatatgga ctatatagat ttacaccctg atcagaaaag ttgtgaagct   1920
tataattcag cattgcatgg atataataca agattagagt tacagaagga atataacagg   1980
atttttgaat cacatgaatc agcatctcca aatgaaatta atagttttc acaaaaatat    2040 agagcagcat taagagatgt tgcgcaggat attgttaatc agggtccaat gttttattct   2100
tctagagatg caatgctatt aagggctaga gtagacacat tgtgtgatat gtgtcgttca   2160
atacgtaatc tgtatatggt tgaattagat gccatagata agaagaaaa atcgttacaa    2220 tctgatatga atctgcaag ttctagtgat aaaaagttga taagaaaa aataaaatta     2280 ctt                                                                2283
```

<210> SEQ ID NO 8
<211> LENGTH: 761
<212> TYPE: PRT
<213> ORGANISM: Ehrlichia canis

<400> SEQUENCE: 8

```
Val Lys Lys Leu Arg Leu Leu Asn Ser Ile Ser Glu Leu Pro Gln
 1               5                  10                  15

Glu Leu Lys Asp Gln Ile Leu Ser Thr Arg Ser Thr Ile Asp Lys Leu
                20                  25                  30

Arg Asn Arg Ile Asn Ala Cys Ile Lys Ser Asp Asp Arg Glu Gly Ile
            35                  40                  45

Ala His Ala Val Glu Ser Met Ala Ser Ser Tyr Cys Glu Leu Leu Gly
        50                  55                  60

His Cys Arg Leu Ile Phe Lys Lys Leu Tyr Asp Glu Asn Ala Asp Lys
 65                  70                  75                  80

Ser Leu Leu Glu Leu Cys Ile Lys Glu Tyr Gln Ser Asp Leu Asn Lys
                85                  90                  95

Leu Leu Glu Gln Gly Ile Asp Ile Cys Ala Ser Glu Val Ser Ser Glu
            100                 105                 110

Cys Lys Asp Leu Val Cys Lys Val Cys Glu Asp Glu Phe Glu Lys Tyr
        115                 120                 125

Asp Ser Leu Ser Lys Val Gln Arg Phe Arg Glu Leu Ser Gly Glu Ile
    130                 135                 140

Ala Asp Leu Asp Asp Lys Leu Thr Arg Arg Ala Ser Phe Val Glu Thr
145                 150                 155                 160

Phe Gly Leu Phe Ser Ser Arg Leu Arg His Tyr Arg Glu Ile Leu Gly
                165                 170                 175

Asp Gly Asp Leu Lys Phe Arg Gly Arg Ile Val Glu Lys Tyr Gln Glu
            180                 185                 190

Asp Leu Lys Glu Leu Leu Glu Leu Ser Val Asp Leu His Leu Leu Ile
        195                 200                 205

Asn Leu Pro Ala Leu Glu Asp Leu Arg Asp His Arg Asn Leu Val His
    210                 215                 220

Arg Ala Cys Asn Ala Glu Ile Glu Lys Tyr Leu Thr Leu Phe Asp Asp
225                 230                 235                 240

Gln Gln Leu Arg Thr Leu Ser Gln Glu Val Asn Asn Ala His Gly Glu
                245                 250                 255

Leu Ile Gln Met Phe Ser Lys Phe Ser Ile Phe Val Asp Gly Val Thr
```

```
                260             265             270
Gly Ile Glu Gln Ser Thr Ser Gln Val Glu His Pro Arg Ser Asp Ile
            275                 280             285
Ala Lys Arg Asp Thr Thr Thr Pro Lys Gln Arg Val Val Gln Gly Lys
        290                 295             300
Asp Asp Ile Gln Ser Ser Asp Ser Asp Ser Asp Ser Asp Ser Lys Tyr
305             310              315              320
Gly Asp Asp Asp Ser Lys Lys Ala Ser Val Ser Ala Pro Ala Val Asp
                325             330              335
Gln Val Val Pro Val Ala Asp Val Gln Pro Glu Pro Gln Leu Gly Glu
            340             345             350
Gly Leu Glu Thr Leu Glu Ser Ser Ile Ala Glu Gly Pro Glu Leu Pro
            355             360             365
Gly Asp Ala Ser Thr Ala Lys Gln Ser Ile Pro Phe Ala Ile Thr Pro
        370             375             380
Ser Ser Pro Glu Thr Val Asp Glu Lys Leu Glu Ser Ser Gly Val Ser
385             390             395             400
Gln Asp Gly Ile Thr Thr Pro Gly Gln Arg Val Val Gln Gly Lys Asp
                405             410             415
Asp Ile Gln Ser Ser Asp Ser Asp Ser Asp Ser Lys Tyr Gly Asp Asp
            420             425             430
Asp Ser Lys Lys Ala Ser Ala Ser Ala Pro Ala Val Asp Gln Val Val
        435             440             445
Pro Val Ala Asp Val Gln Pro Glu Pro Gln Leu Gly Glu Lys Leu Glu
        450             455             460
Thr Leu Glu Ser Ser Ile Thr Lys Gly Pro Glu Leu Pro Gly Asp Ala
465             470             475             480
Ser Thr Ala Lys Gln Ser Ile Pro Phe Ala Ile Thr Pro Ser Ser Pro
                485             490             495
Glu Thr Val Asp Glu Lys Leu Ser Ser Gly Val Ser Gln Asp Gly
                500             505             510
Ile Thr Thr Pro Gly Gln Arg Val Val Gln Gly Lys Asp Asp Ile Gln
            515             520             525
Ser Ser Asp Ser Asp Ser Asp Ser Lys Tyr Gly Asp Asp Asp Ser Lys
        530             535             540
Lys Ala Ser Ala Ser Ala Pro Ala Val Asp Gln Val Val Pro Ser Asp
545             550             555             560
Thr Arg Ala Asp Gly Val Ser Glu Pro Leu Ala Ser His Val Asp Gln
                565             570             575
Gly Ser Asp Val Pro Gly Asp Ala Ser Val Asp Gly Val Asp Leu Arg
            580             585             590
Leu Gly Arg Leu Ser Thr Glu Gln Ser Gly Leu Leu Pro Arg His Glu
            595             600             605
Gln Asn Val Arg Ala Phe Ile Leu Glu Gln Ser Leu Leu Asp Gln Leu
        610             615             620
Tyr Met Asp Tyr Ile Asp Leu His Pro Asp Gln Lys Ser Cys Glu Ala
625             630             635             640
Tyr Asn Ser Ala Leu His Gly Tyr Asn Thr Arg Leu Glu Leu Gln Lys
                645             650             655
Glu Tyr Asn Arg Ile Phe Glu Ser His Glu Ser Ala Ser Pro Asn Glu
            660             665             670
Ile Asn Ser Phe Ser Gln Lys Tyr Arg Ala Ala Leu Arg Asp Val Ala
        675             680             685
```

```
Gln Asp Ile Val Asn Gln Gly Pro Met Phe Tyr Ser Ser Arg Asp Ala
    690                 695                 700

Met Leu Leu Arg Ala Arg Val Asp Thr Leu Cys Asp Met Cys Arg Ser
705                 710                 715                 720

Ile Arg Asn Leu Tyr Met Val Glu Leu Asp Ala Ile Asp Lys Glu Glu
                725                 730                 735

Lys Ser Leu Gln Ser Asp Met Lys Ser Ala Ser Ser Ser Asp Lys Lys
            740                 745                 750

Leu Ile Gln Glu Lys Ile Lys Leu Leu
        755                 760

<210> SEQ ID NO 9
<211> LENGTH: 414
<212> TYPE: DNA
<213> ORGANISM: Ehrlichia canis
<400> SEQUENCE: 9
atgttacacg ttcaaaatca tgttgatcaa catacaaatc atatagaaca tgatgattac     60
cattttactg gtcctactag ttttgaagtt aatctttctg aagaagaaaa aatggagtta    120
caagaagtat cttctattga tagtgtagga tgcgaagatt gtgatccaaa ttgtcgttat    180
cctttagaat tagtagaatg tcagcgtatt gaggaaagac cagtatgcaa tgcaggttta    240
gagagcttga ctgttgatgc atatcaatta ggattgttgt taggtggttt tttaagtgct    300
atgaattaca tatcttatag ctatccttgt tattattatg attgttgtga tagaaattat    360
tacgactgtt gtcataagaa tgcgtgttat tacaactgtt gtgattgtgc gtaa          414

<210> SEQ ID NO 10
<211> LENGTH: 137
<212> TYPE: PRT
<213> ORGANISM: Ehrlichia canis

<400> SEQUENCE: 10

Met Leu His Val Gln Asn His Val Asp Gln His Thr Asn His Ile Glu
1               5                   10                  15

His Asp Asp Tyr His Phe Thr Gly Pro Thr Ser Phe Glu Val Asn Leu
            20                  25                  30

Ser Glu Glu Glu Lys Met Glu Leu Gln Glu Val Ser Ser Ile Asp Ser
        35                  40                  45

Val Gly Cys Glu Asp Cys Asp Pro Asn Cys Arg Tyr Pro Leu Glu Leu
    50                  55                  60

Val Glu Cys Gln Arg Ile Glu Glu Arg Pro Val Cys Asn Ala Gly Leu
65                  70                  75                  80

Glu Ser Leu Thr Val Asp Ala Tyr Gln Leu Gly Leu Leu Leu Gly Gly
                85                  90                  95

Phe Leu Ser Ala Met Asn Tyr Ile Ser Tyr Ser Tyr Pro Cys Tyr Tyr
            100                 105                 110

Tyr Asp Cys Cys Asp Arg Asn Tyr Tyr Asp Cys Cys His Lys Asn Ala
        115                 120                 125

Cys Tyr Tyr Asn Cys Cys Asp Cys Ala
    130                 135

<210> SEQ ID NO 11
<211> LENGTH: 3018
<212> TYPE: DNA
<213> ORGANISM: Ehrlichia canis

<400> SEQUENCE: 11
```

-continued

| | |
|---|---|
| atgacgattt tcttagaaag tgatgatgat aagagtaact ttaagaagac attggagaac | 60 |
| ggtactaaag acaagacaaa tctagataat acttattatg actatcatca tgaagatgat | 120 |
| atgggaaata ctgaatatca ttatgtgagt ttggatagag tggatcatgt taagatgcct | 180 |
| gaagagcctg taggttatgg tggagatact ttacctattg ttcctactac agctgctagt | 240 |
| gtatctggta gtgatgcagg cgttgctgta ggtaatgtta agattttga agataatgtt | 300 |
| tttcatcata catctactat aagaaacgat gaattgaaga tagatttacg aatacatact | 360 |
| ttaaaggatt tatctgataa aagattacgt gaaattgaaa agggatttaa tgatacggta | 420 |
| acaaaattta aaaataattt tggggttagaa ccaaatgatg agaaactat ttttgattta | 480 |
| tacctttttg atgataagga acaatataat tattatggaa agctttataa cttaggaatt | 540 |
| agtggatctg gaggtatgac tttctatgga aatgctaatg ttccatataa aatttatgta | 600 |
| catcaatatg gtgaaatatt gaatttaaaa catgaattaa ctcatgcatt agaaagttat | 660 |
| gcatctggac ataaattgca tggttctgac gtaaatagca gaatatttac ggaaggatta | 720 |
| gctgattata tccaagaaga taatagtttt attatgagag gattaaagga tcgagagatc | 780 |
| acttcagatg tattgaaaga ttcttctggt aatgtagatc atttaagtgg tgttgcagtg | 840 |
| aatgaaaatc agaggttaag ttatagtata ggacatgcat ttgtaagctt tttacaagag | 900 |
| aaatatccta agttaatttc ggaatattta aacgcattaa aagaggataa tattattcgt | 960 |
| gctaaagaaa taattagtat ggataagtat ccagattttg agccgtgggt gaagtctaaa | 1020 |
| gacattagtt tatatttaga aaatatgaat gtattaaagt taggattagg tgagaaaatg | 1080 |
| ttttctgctg aaagtgctag ctattttgaa gatcaaggtg tcaataaaga atattaccat | 1140 |
| gaaaatattt atgatatgag tggtaaaacta gtaggtgaaa tgtcacctgt agtgcattat | 1200 |
| gcacaaaaaa atgtgattcg tatttggaat attgcaagtc ctgatatgat agaggtgcga | 1260 |
| ccagaatata actttctgaa attggtaact actccatctg gtaagtctgc atatgtatat | 1320 |
| tgtgataaga atgggcatga gtattttaat actaaagatt acatagattc tgcgtttaat | 1380 |
| atattggcaa gatatgatgt taagcttcgt gaaagtagtg atgctttgga tattagaggt | 1440 |
| cgttactcag atgctgctaa agtgtttagt aagctgccta atgcggattt gctgttggat | 1500 |
| aagttttag aaaaaatagg ttatagtagt tataagcaga taataatgag taatccagaa | 1560 |
| cagcttaatt ctattaaggc ttatgtagta aaagaagtgt ttgaaaattt tagggaatct | 1620 |
| gaggtcaaaa aggtgttgag tggtgagtct catccggaag taagaaatgt attaatggat | 1680 |
| cttacctatg ttgatttaaa gagtgttata ggagtaaatg gtgcagatat tgacagtatt | 1740 |
| atttctaatc cagatgtaat gttgcgtact gctgtgttag gtaaaggaaa tgcaagtggg | 1800 |
| atatctctat atgtagatga tcagaaagtt ggtgagctgt caactgaagc aggttattgt | 1860 |
| gttaaaaatc ttgatactgg taaagtgtat tttatgttcc ataatgttgt tggaatgata | 1920 |
| gcaagtggtt atgaagacag agcatatatg gttgtattag aaaagatgg taagtttact | 1980 |
| actgctctag ttaataatat acaaaaagca gcagatggaa atgttgtatg ggataatcaa | 2040 |
| tttaatcatc cgaatattaa taacttgcac tcaaattata aggagctgtt gttaaatgat | 2100 |
| gcttcagtta aagattactc tcatcttgcg gatgtgaaat ttaataaaga tgatacagta | 2160 |
| attgttaaag gtgaattatt agatgataaa ggtactgtaa gtgtagatga tgatgtacat | 2220 |
| cgtgcagttg ttaagcatga tgatcaaata ctacatcagt ttaagagtat gtctttttac | 2280 |
| attactgaac catcagctga ttcaggtgac aattatggaa gtgatttttt catttctgat | 2340 |
| gaaggaaaaa atcttagatt tcaacttcct aaagctatta cgcatttgaa attggttaat | 2400 |

-continued

```
gttaatggaa ataataagtt ggtaccatgt actaaagatg ggaatgaaca tcctgaaggt 2460
atgccatctg atttaacgga tgaatataga tatatagatc ctatttttgc tcatacattt 2520
gagaaacaaa gttattctaa aaatagtatt agtgttgggt tagtggactt cagtaaatat 2580
aaagaaggat ctatgtttaa attacagcat tattctgatg attatcatat tcataaggat 2640
gaacaaggta atgttattag gcctaataac agatcttacg ttacaaaagt ggatttagta 2700
tatgatgata aagttattgg gatgttgtct gatagtataa atcaatttca gggtgatatt 2760
ttcatttctg caagccttaa ttatagccac aatgattttc tttcatctaa gtactttcag 2820
aaagttaata ttgaggcgtt agaaaatgga atatatagtg gaagatatga tgtaggagat 2880
ggtgaccaaa tagcaggtct taatactgat acaggttata gtgataaagc tatttttttac 2940
tttaaaaatg atagcgcatc tactgatatg ccggctagtg atgttactac tattttacct 3000
tatataaatg agctttaa 3018
```

<210> SEQ ID NO 12
<211> LENGTH: 1005
<212> TYPE: PRT
<213> ORGANISM: Ehrlichia canis

<400> SEQUENCE: 12

```
Met Thr Ile Phe Leu Glu Ser Asp Asp Asp Lys Ser Asn Phe Lys Lys
1               5                   10                  15

Thr Leu Glu Asn Gly Thr Lys Asp Lys Thr Asn Leu Asp Asn Thr Tyr
            20                  25                  30

Tyr Asp Tyr His His Glu Asp Asp Met Gly Asn Thr Glu Tyr His Tyr
        35                  40                  45

Val Ser Leu Asp Arg Val Asp His Val Lys Met Pro Glu Glu Pro Val
    50                  55                  60

Gly Tyr Gly Gly Asp Thr Leu Pro Ile Val Pro Thr Thr Ala Ala Ser
65                  70                  75                  80

Val Ser Gly Ser Asp Ala Gly Val Ala Val Gly Asn Val Lys Asp Phe
                85                  90                  95

Glu Asp Asn Val Phe His His Thr Ser Thr Ile Arg Asn Asp Glu Leu
            100                 105                 110

Lys Ile Asp Leu Arg Ile His Thr Leu Lys Asp Leu Ser Asp Lys Arg
        115                 120                 125

Leu Arg Glu Ile Glu Lys Gly Phe Asn Asp Thr Val Thr Lys Phe Lys
    130                 135                 140

Asn Asn Phe Gly Leu Glu Pro Asn Asp Gly Glu Thr Ile Phe Asp Leu
145                 150                 155                 160

Tyr Leu Phe Asp Asp Lys Glu Gln Tyr Asn Tyr Tyr Gly Lys Leu Tyr
                165                 170                 175

Asn Leu Gly Ile Ser Gly Ser Gly Gly Met Thr Phe Tyr Gly Asn Ala
            180                 185                 190

Asn Val Pro Tyr Lys Ile Tyr Val His Gln Tyr Gly Glu Ile Leu Asn
        195                 200                 205

Leu Lys His Glu Leu Thr His Ala Leu Glu Ser Tyr Ala Ser Gly His
    210                 215                 220

Lys Leu His Gly Ser Asp Val Asn Ser Arg Ile Phe Thr Glu Gly Leu
225                 230                 235                 240

Ala Asp Tyr Ile Gln Glu Asp Asn Ser Phe Ile Met Arg Gly Leu Lys
                245                 250                 255

Asp Arg Glu Ile Thr Ser Asp Val Leu Lys Asp Ser Ser Gly Asn Val
            260                 265                 270
```

```
Asp His Leu Ser Gly Val Ala Val Asn Glu Asn Gln Arg Leu Ser Tyr
        275                 280                 285

Ser Ile Gly His Ala Phe Val Ser Phe Leu Gln Glu Lys Tyr Pro Lys
        290                 295                 300

Leu Ile Ser Glu Tyr Leu Asn Ala Leu Lys Glu Asp Asn Ile Ile Arg
305                 310                 315                 320

Ala Lys Glu Ile Ile Ser Met Asp Lys Tyr Pro Asp Phe Glu Pro Trp
                325                 330                 335

Val Lys Ser Lys Asp Ile Ser Leu Tyr Leu Glu Asn Met Asn Val Leu
            340                 345                 350

Lys Leu Gly Leu Gly Glu Lys Met Phe Ser Ala Glu Ser Ala Ser Tyr
        355                 360                 365

Phe Glu Asp Gln Gly Val Asn Lys Glu Tyr Tyr His Glu Asn Ile Tyr
        370                 375                 380

Asp Met Ser Gly Lys Leu Val Gly Glu Met Ser Pro Val Val His Tyr
385                 390                 395                 400

Ala Gln Lys Asn Val Ile Arg Ile Trp Asn Ile Ala Ser Pro Asp Met
                405                 410                 415

Ile Glu Val Arg Pro Glu Tyr Asn Phe Leu Lys Leu Val Thr Thr Pro
            420                 425                 430

Ser Gly Lys Ser Ala Tyr Val Tyr Cys Asp Lys Asn Gly His Glu Tyr
        435                 440                 445

Phe Asn Thr Lys Asp Tyr Ile Asp Ser Ala Phe Asn Ile Leu Ala Arg
        450                 455                 460

Tyr Asp Val Lys Leu Arg Glu Ser Ser Asp Ala Leu Asp Ile Arg Gly
465                 470                 475                 480

Arg Tyr Ser Asp Ala Ala Lys Val Phe Ser Lys Leu Pro Asn Ala Asp
                485                 490                 495

Leu Leu Leu Asp Lys Phe Leu Glu Lys Ile Gly Tyr Ser Ser Tyr Lys
            500                 505                 510

Gln Ile Ile Met Ser Asn Pro Glu Gln Leu Asn Ser Ile Lys Ala Tyr
        515                 520                 525

Val Val Lys Glu Val Phe Glu Asn Phe Arg Glu Ser Glu Val Lys Lys
        530                 535                 540

Val Leu Ser Gly Glu Ser His Pro Glu Val Arg Asn Val Leu Met Asp
545                 550                 555                 560

Leu Thr Tyr Val Asp Leu Lys Ser Val Ile Gly Val Asn Gly Ala Asp
                565                 570                 575

Ile Asp Ser Ile Ile Ser Asn Pro Asp Val Met Leu Arg Thr Ala Val
            580                 585                 590

Leu Gly Lys Gly Asn Ala Ser Gly Ile Ser Leu Tyr Val Asp Asp Gln
        595                 600                 605

Lys Val Gly Glu Leu Ser Thr Glu Ala Gly Tyr Cys Val Lys Asn Leu
        610                 615                 620

Asp Thr Gly Lys Val Tyr Phe Met Phe His Asn Val Val Gly Met Ile
625                 630                 635                 640

Ala Ser Gly Tyr Glu Asp Arg Ala Tyr Met Val Val Leu Glu Lys Asp
                645                 650                 655

Gly Lys Phe Thr Thr Ala Leu Val Asn Asn Ile Gln Lys Ala Ala Asp
            660                 665                 670

Gly Asn Val Val Trp Asp Asn Gln Phe Asn His Pro Asn Ile Asn Asn
        675                 680                 685

Leu His Ser Asn Tyr Lys Glu Leu Leu Leu Asn Asp Ala Ser Val Lys
```

|     |     |     |     |     |     |     |     |     |     |     |     |
| --- | --- | --- | --- | --- | --- | --- | --- | --- | --- | --- | --- |
|     |     | 690 |     |     | 695 |     |     | 700 |     |     |     |
| Asp | Tyr | Ser | His | Leu | Ala | Asp | Val | Lys | Phe | Asn | Lys | Asp | Asp | Thr | Val |
| 705 |     |     |     | 710 |     |     |     | 715 |     |     |     | 720 |
| Ile | Val | Lys | Gly | Glu | Leu | Leu | Asp | Asp | Lys | Gly | Thr | Val | Ser | Val | Asp |
|     |     |     |     | 725 |     |     |     |     | 730 |     |     |     |     | 735 |
| Asp | Asp | Val | His | Arg | Ala | Val | Val | Lys | His | Asp | Asp | Gln | Ile | Leu | His |
|     |     |     | 740 |     |     |     |     | 745 |     |     |     |     | 750 |
| Gln | Phe | Lys | Ser | Met | Ser | Phe | Tyr | Ile | Thr | Glu | Pro | Ser | Ala | Asp | Ser |
|     |     | 755 |     |     |     |     | 760 |     |     |     |     | 765 |
| Gly | Asp | Asn | Tyr | Gly | Ser | Asp | Phe | Ile | Ser | Asp | Glu | Gly | Lys | Asn |
|     | 770 |     |     |     |     | 775 |     |     |     |     | 780 |
| Leu | Arg | Phe | Gln | Leu | Pro | Lys | Ala | Ile | Thr | His | Leu | Lys | Leu | Val | Asn |
| 785 |     |     |     | 790 |     |     |     |     | 795 |     |     |     |     | 800 |
| Val | Asn | Gly | Asn | Asn | Lys | Leu | Val | Pro | Cys | Thr | Lys | Asp | Gly | Asn | Glu |
|     |     |     |     | 805 |     |     |     |     | 810 |     |     |     |     | 815 |
| His | Pro | Glu | Gly | Met | Pro | Ser | Asp | Leu | Thr | Asp | Glu | Tyr | Arg | Tyr | Ile |
|     |     |     | 820 |     |     |     |     | 825 |     |     |     |     | 830 |
| Asp | Pro | Ile | Phe | Ala | His | Thr | Phe | Glu | Lys | Gln | Ser | Tyr | Ser | Lys | Asn |
|     |     | 835 |     |     |     |     | 840 |     |     |     |     | 845 |
| Ser | Ile | Ser | Val | Gly | Leu | Val | Asp | Phe | Ser | Lys | Tyr | Lys | Glu | Gly | Ser |
| 850 |     |     |     |     | 855 |     |     |     |     | 860 |
| Met | Phe | Lys | Leu | Gln | His | Tyr | Ser | Asp | Asp | Tyr | His | Ile | His | Lys | Asp |
| 865 |     |     |     |     | 870 |     |     |     |     | 875 |     |     |     |     | 880 |
| Glu | Gln | Gly | Asn | Val | Ile | Arg | Pro | Asn | Asn | Arg | Ser | Tyr | Val | Thr | Lys |
|     |     |     |     | 885 |     |     |     |     | 890 |     |     |     |     | 895 |
| Val | Asp | Leu | Val | Tyr | Asp | Asp | Lys | Val | Ile | Gly | Met | Leu | Ser | Asp | Ser |
|     |     |     | 900 |     |     |     |     | 905 |     |     |     |     | 910 |
| Ile | Asn | Gln | Phe | Gln | Gly | Asp | Ile | Phe | Ile | Ser | Ala | Ser | Leu | Asn | Tyr |
|     |     | 915 |     |     |     |     | 920 |     |     |     |     | 925 |
| Ser | His | Asn | Asp | Phe | Leu | Ser | Ser | Lys | Tyr | Phe | Gln | Lys | Val | Asn | Ile |
|     | 930 |     |     |     |     | 935 |     |     |     |     | 940 |
| Glu | Ala | Leu | Glu | Asn | Gly | Ile | Tyr | Ser | Gly | Arg | Tyr | Asp | Val | Gly | Asp |
| 945 |     |     |     |     | 950 |     |     |     |     | 955 |     |     |     |     | 960 |
| Gly | Asp | Gln | Ile | Ala | Gly | Leu | Asn | Thr | Asp | Thr | Gly | Tyr | Ser | Asp | Lys |
|     |     |     |     | 965 |     |     |     |     | 970 |     |     |     |     | 975 |
| Ala | Ile | Phe | Tyr | Phe | Lys | Asn | Asp | Ser | Ala | Ser | Thr | Asp | Met | Pro | Ala |
|     |     |     | 980 |     |     |     |     | 985 |     |     |     |     | 990 |
| Ser | Asp | Val | Thr | Thr | Ile | Leu | Pro | Tyr | Ile | Asn | Glu | Leu |
|     |     | 995 |     |     |     |     | 1000 |     |     |     |     | 1005 |

<210> SEQ ID NO 13
<211> LENGTH: 2172
<212> TYPE: DNA
<213> ORGANISM: Ehrlichia canis

<400> SEQUENCE: 13

```
atggatagta taagtgcaaa tcacatacgc aatattttat tccttgtttt aggcgcattt      60
tttggactgg aattttgctt ttatttatca ggtgtattat tcatcttaat ggtctgggga     120
ccaaattacc tagattttaa tgctataaat cccagtttga gtgattttcc agacagaatt     180
tggccaacta tttttgacta tgtacaacat ggtggaaga acccttctgc atacgatgca     240
gttttattac ttaagctaat aacgtcatta tgtacaccag taggtattct aagcatagta     300
ttatggaacc ttagaaatat attattcgat tggaggccat ttaagaagaa agaatcactg     360
catggagatt caagatgggc aacagaaaaa gatattcgca aaataggatt acgtagtaga     420
```

-continued

```
aaaggaatat tattagggaa agacaagaga ggatatctca ttgcagatgg atatcaacat    480
gcattgttat ttgcaccaac tggatccgga aaaggtgtag gttttgtaat accaaactta    540
ttattctggg aagattctgt agtagtacac gatataaaat tagagaacta tgatcttaca    600
agtgggtgga gaaaaaaaag gggacaagaa gttttcgtgt ggaacccagc acaacctgac    660
ggtataagtc actgttacaa cccattagat tggataagct ctaagcctgg acaaatggta    720
gatgatgtac aaaaaattgc caatctaata atgcctgaac aagatttttg gtataacgaa    780
gcacgtagtt tatttgtagg agtagtatta tacttactag cagtaccaga aaaagtaaaa    840
tcctttggag aagttgtaag aacaatgcgc agcgatgacg tagtctacaa cttagcagta    900
gtactagaca caatagggaa aaagattcac ccagttgcat acatgaatat agctgcattt    960
ttacaaaaag cagacaaaga acgctcaggt gttgtatcaa ctatgaactc atctttagaa   1020
ttatgggcaa acccattaat agatacagca acagcatcaa gtgattttaa tattcaagaa   1080
tttaaaagga aaaaagtaac agtatatgtt ggattaacac cagataattt aactcgtctt   1140
agacctttaa tgcaggtatt ttatcaacaa gctacagaat ttttatgtag aactttacca   1200
tcagatgatg aaccatatgg tgtactgttc ttaatggatg agtttccaac attaggaaaa   1260
atggagcaat ttcaaacagg tatcgcatat ttccgtggat atagagttag actatttttg   1320
attattcaag atactgaaca gcttaagggt atatatgaag aagcaggaat gaactcattc   1380
ttatcaaact ctacttatag aataactttt gctgcaaata atatagaaac tgcaaattta   1440
atatcacagt taataggaaa taaaactgtt aaccaagagt ctttaaacag acctaaattt   1500
ttagatttga accctgcatc acgttcatta catatatcag aaacacaaag agctttacta   1560
ttacctcaag aagtaataat gttacccaga gatgagcaaa tacttttaat agaatctact   1620
tatcctataa aatcaaagaa aataaaatac tatgaagaca aaaattttac aaaaaaacta   1680
ttaaagagta cctttgttcc aactcaagag ccttatgatc ccaacaaaac aaaaacagca   1740
acaaaagaaa acgaagaacc tatgccaagt attgaaagcg atcttcctaa aaatacatct   1800
gacaatactg aaaacaatat ggaagatggt gcaatgtaca gcagcataga agaagattat   1860
gacgatgatg atgatgattt taattttgaa gacttagatg aatatatgga tgaagaagaa   1920
gattatgatg atgaagaata tgatgatata gattatgatg ataataacaa tagtaatgag   1980
gagtatgaag aagataatcc agaagaagat gacaatagca ataatctaga cgatgaggaa   2040
gaggaagaag ataatattat agattatgaa gatgaagaag aatatgatga taacatagac   2100
tacaaagatg atgacaataa ctacaacaaa gataccactg acgatcaaga ctcaaaaaaa   2160
cataatgaat ag                                                       2172
```

<210> SEQ ID NO 14
<211> LENGTH: 723
<212> TYPE: PRT
<213> ORGANISM: Ehrlichia canis

<400> SEQUENCE: 14

```
Met Asp Ser Ile Ser Ala Asn His Ile Arg Asn Ile Leu Phe Leu Val
1               5                   10                  15

Leu Gly Ala Phe Phe Gly Leu Glu Phe Cys Phe Tyr Leu Ser Gly Val
            20                  25                  30

Leu Phe Ile Leu Met Val Trp Gly Pro Asn Tyr Leu Asp Phe Asn Ala
        35                  40                  45

Ile Asn Pro Ser Leu Ser Asp Phe Pro Asp Arg Ile Trp Pro Thr Ile
    50                  55                  60
```

```
Phe Asp Tyr Val Gln His Trp Lys Asn Pro Ser Ala Tyr Asp Ala
 65                  70                  75                  80

Val Leu Leu Leu Lys Leu Ile Thr Ser Leu Cys Thr Pro Val Gly Ile
             85                  90                  95

Leu Ser Ile Val Leu Trp Asn Leu Arg Asn Ile Leu Phe Asp Trp Arg
            100                 105                 110

Pro Phe Lys Lys Glu Ser Leu His Gly Asp Ser Arg Trp Ala Thr
        115                 120                 125

Glu Lys Asp Ile Arg Lys Ile Gly Leu Arg Ser Arg Lys Gly Ile Leu
    130                 135                 140

Leu Gly Lys Asp Lys Arg Gly Tyr Leu Ile Ala Asp Gly Tyr Gln His
145                 150                 155                 160

Ala Leu Leu Phe Ala Pro Thr Gly Ser Gly Lys Gly Val Gly Phe Val
                165                 170                 175

Ile Pro Asn Leu Leu Phe Trp Glu Asp Ser Val Val His Asp Ile
                180                 185                 190

Lys Leu Glu Asn Tyr Asp Leu Thr Ser Gly Trp Arg Lys Lys Arg Gly
        195                 200                 205

Gln Glu Val Phe Val Trp Asn Pro Ala Gln Pro Asp Gly Ile Ser His
    210                 215                 220

Cys Tyr Asn Pro Leu Asp Trp Ile Ser Ser Lys Pro Gly Gln Met Val
225                 230                 235                 240

Asp Asp Val Gln Lys Ile Ala Asn Leu Ile Met Pro Glu Gln Asp Phe
                245                 250                 255

Trp Tyr Asn Glu Ala Arg Ser Leu Phe Val Gly Val Leu Tyr Leu
                260                 265                 270

Leu Ala Val Pro Glu Lys Val Lys Ser Phe Gly Glu Val Val Arg Thr
                275                 280                 285

Met Arg Ser Asp Asp Val Val Tyr Asn Leu Ala Val Val Leu Asp Thr
    290                 295                 300

Ile Gly Lys Lys Ile His Pro Val Ala Tyr Met Asn Ile Ala Ala Phe
305                 310                 315                 320

Leu Gln Lys Ala Asp Lys Glu Arg Ser Gly Val Val Ser Thr Met Asn
                325                 330                 335

Ser Ser Leu Glu Leu Trp Ala Asn Pro Leu Ile Asp Thr Ala Thr Ala
            340                 345                 350

Ser Ser Asp Phe Asn Ile Gln Glu Phe Lys Arg Lys Val Thr Val
        355                 360                 365

Tyr Val Gly Leu Thr Pro Asp Asn Leu Thr Arg Leu Arg Pro Leu Met
370                 375                 380

Gln Val Phe Tyr Gln Ala Thr Glu Phe Leu Cys Arg Thr Leu Pro
385                 390                 395                 400

Ser Asp Asp Glu Pro Tyr Gly Val Leu Phe Leu Met Asp Glu Phe Pro
                405                 410                 415

Thr Leu Gly Lys Met Glu Gln Phe Gln Thr Gly Ile Ala Tyr Phe Arg
            420                 425                 430

Gly Tyr Arg Val Arg Leu Phe Leu Ile Ile Gln Asp Thr Glu Gln Leu
        435                 440                 445

Lys Gly Ile Tyr Glu Glu Ala Gly Met Asn Ser Phe Leu Ser Asn Ser
    450                 455                 460

Thr Tyr Arg Ile Thr Phe Ala Ala Asn Asn Ile Glu Thr Ala Asn Leu
465                 470                 475                 480

Ile Ser Gln Leu Ile Gly Asn Lys Thr Val Asn Gln Glu Ser Leu Asn
```

```
                     485                 490                 495
Arg Pro Lys Phe Leu Asp Leu Asn Pro Ala Ser Arg Ser Leu His Ile
                500                 505                 510

Ser Glu Thr Gln Arg Ala Leu Leu Pro Gln Glu Val Ile Met Leu
            515                 520                 525

Pro Arg Asp Glu Gln Ile Leu Leu Ile Glu Ser Thr Tyr Pro Ile Lys
        530                 535                 540

Ser Lys Lys Ile Lys Tyr Tyr Glu Asp Lys Asn Phe Thr Lys Lys Leu
545                 550                 555                 560

Leu Lys Ser Thr Phe Val Pro Thr Gln Glu Pro Tyr Asp Pro Asn Lys
                565                 570                 575

Thr Lys Thr Ala Thr Lys Glu Asn Glu Glu Pro Met Pro Ser Ile Glu
            580                 585                 590

Ser Asp Leu Pro Lys Asn Thr Ser Asp Asn Thr Glu Asn Asn Met Glu
        595                 600                 605

Asp Gly Ala Met Tyr Ser Ser Ile Glu Glu Asp Tyr Asp Asp Asp
    610                 615                 620

Asp Asp Phe Asn Phe Glu Asp Leu Asp Glu Tyr Met Asp Glu Glu Glu
625                 630                 635                 640

Asp Tyr Asp Asp Glu Glu Tyr Asp Asp Ile Asp Tyr Asp Asp Asn Asn
                645                 650                 655

Asn Ser Asn Glu Glu Tyr Glu Glu Asp Asn Pro Glu Glu Asp Asp Asn
            660                 665                 670

Ser Asn Asn Leu Asp Asp Glu Glu Glu Glu Asp Asn Ile Ile Asp
        675                 680                 685

Tyr Glu Asp Glu Glu Glu Tyr Asp Asp Asn Ile Asp Tyr Lys Asp Asp
690                 695                 700

Asp Asn Asn Tyr Asn Lys Asp Thr Thr Asp Asp Gln Asp Ser Lys Lys
705                 710                 715                 720

His Asn Glu

<210> SEQ ID NO 15
<211> LENGTH: 688
<212> TYPE: PRT
<213> ORGANISM: Ehrlichia canis

<400> SEQUENCE: 15

Met Asp Ile Asp Asn Asn Asn Val Thr Thr Ser Ser Thr Gln Asp Lys
1               5                   10                  15

Ser Gly Asn Leu Met Glu Val Ile Met Arg Ile Leu Asn Phe Gly Asn
            20                  25                  30

Asn Ser Asp Glu Lys Val Ser Asn Glu Asp Thr Lys Val Leu Val Glu
        35                  40                  45

Ser Leu Gln Pro Ala Val Asn Asp Asn Val Gly Asn Pro Ser Ser Glu
    50                  55                  60

Val Gly Lys Glu Glu Asn Ala Pro Glu Val Lys Ala Glu Asp Leu Gln
65                  70                  75                  80

Pro Ala Val Asp Gly Ser Val Glu His Ser Ser Glu Val Gly Lys
                85                  90                  95

Lys Val Ser Glu Thr Ser Lys Glu Glu Ser Thr Pro Glu Val Lys Ala
            100                 105                 110

Glu Asp Leu Gln Pro Ala Val Asp Gly Ser Ile Glu His Ser Ser Ser
        115                 120                 125

Glu Val Gly Glu Lys Val Ser Lys Thr Ser Lys Glu Glu Ser Thr Pro
    130                 135                 140
```

```
Glu Val Lys Ala Glu Asp Leu Gln Pro Ala Val Asp Ser Val Glu
145                 150                 155                 160

His Ser Ser Glu Val Gly Glu Lys Val Ser Thr Ser Lys Glu
        165                 170                 175

Glu Asn Thr Pro Glu Val Lys Ala Glu Asp Leu Gln Pro Ala Val Asp
            180                 185                 190

Gly Ser Ile Glu His Ser Ser Glu Val Gly Glu Lys Val Ser Lys
        195                 200                 205

Thr Ser Lys Glu Glu Ser Thr Pro Glu Val Lys Ala Glu Asp Leu Gln
        210                 215                 220

Pro Ala Val Asp Asp Ser Val Glu His Ser Ser Glu Val Gly Glu
225                 230                 235                 240

Lys Val Ser Glu Thr Ser Lys Glu Glu Asn Thr Pro Glu Val Lys Ala
                245                 250                 255

Glu Asp Leu Gln Pro Ala Val Asp Gly Ser Val Glu His Ser Ser Ser
            260                 265                 270

Glu Val Gly Glu Lys Val Ser Lys Thr Ser Lys Glu Glu Ser Thr Pro
        275                 280                 285

Glu Val Lys Ala Glu Asp Leu Gln Pro Ala Val Asp Asp Ser Val Glu
        290                 295                 300

His Ser Ser Glu Val Gly Glu Lys Val Ser Glu Thr Ser Lys Glu
305                 310                 315                 320

Glu Asn Thr Pro Glu Val Arg Ala Glu Asp Leu Gln Pro Ala Val Asp
                325                 330                 335

Gly Ser Val Glu His Ser Ser Glu Val Gly Glu Lys Val Ser Glu
            340                 345                 350

Thr Ser Lys Glu Glu Ser Thr Pro Glu Val Lys Ala Glu Asp Leu Gln
        355                 360                 365

Pro Ala Val Asp Ser Ser Ile Glu His Ser Ser Glu Val Gly Lys
370                 375                 380

Lys Val Ser Glu Thr Ser Lys Glu Glu Ser Thr Pro Glu Val Lys Ala
385                 390                 395                 400

Glu Asp Leu Gln Pro Ala Val Asp Gly Ser Val Glu His Ser Ser Ser
            405                 410                 415

Glu Val Gly Glu Lys Val Ser Glu Thr Ser Lys Glu Glu Asn Thr Pro
        420                 425                 430

Glu Val Lys Ala Glu Asp Leu Gln Pro Ala Val Asp Gly Ser Val Glu
        435                 440                 445

His Ser Ser Glu Val Gly Glu Lys Val Ser Glu Thr Ser Lys Glu
450                 455                 460

Glu Asn Thr Pro Glu Val Lys Ala Glu Asp Leu Gln Pro Ala Val Asp
465                 470                 475                 480

Gly Ser Val Glu His Ser Ser Glu Val Gly Glu Lys Val Ser Glu
            485                 490                 495

Thr Ser Lys Glu Glu Ser Thr Pro Glu Val Lys Ala Glu Asp Leu Gln
        500                 505                 510

Pro Ala Val Asp Asp Ser Val Glu His Ser Ser Glu Val Gly Glu
        515                 520                 525

Lys Val Ser Glu Thr Ser Lys Glu Glu Ser Thr Pro Glu Val Lys Ala
530                 535                 540

Glu Asp Leu Gln Pro Ala Val Asp Gly Ser Val Glu His Ser Ser Ser
545                 550                 555                 560

Glu Val Gly Glu Lys Val Ser Glu Thr Ser Lys Glu Glu Ser Thr Pro
```

```
                        565                 570                 575
Glu Val Lys Ala Glu Val Gln Pro Val Ala Asp Gly Asn Pro Val Pro
                580                 585                 590

Leu Asn Pro Met Pro Ser Ile Asp Asn Ile Asp Thr Asn Ile Ile Phe
            595                 600                 605

His Tyr His Lys Asp Cys Lys Lys Gly Ser Ala Val Gly Thr Asp Glu
        610                 615                 620

Met Cys Cys Pro Val Ser Glu Leu Met Ala Gly Glu His Val His Met
625                 630                 635                 640

Tyr Gly Ile Tyr Val Tyr Arg Val Gln Ser Val Lys Asp Leu Ser Gly
                645                 650                 655

Val Phe Asn Ile Asp His Ser Thr Cys Asp Cys Asn Leu Asp Val Tyr
                660                 665                 670

Phe Val Gly Tyr Asn Ser Phe Thr Asn Lys Glu Thr Val Asp Leu Ile
                675                 680                 685

<210> SEQ ID NO 16
<211> LENGTH: 515
<212> TYPE: PRT
<213> ORGANISM: Ehrlichia canis

<400> SEQUENCE: 16

Lys Glu Glu Asn Ala Pro Glu Val Lys Ala Glu Asp Leu Gln Pro Ala
1               5                   10                  15

Val Asp Gly Ser Val Glu His Ser Ser Ser Glu Val Gly Lys Lys Val
            20                  25                  30

Ser Glu Thr Ser Lys Glu Glu Ser Thr Pro Glu Val Lys Ala Glu Asp
        35                  40                  45

Leu Gln Pro Ala Val Asp Gly Ser Ile Glu His Ser Ser Ser Glu Val
    50                  55                  60

Gly Glu Lys Val Ser Lys Thr Ser Lys Glu Glu Ser Thr Pro Glu Val
65                  70                  75                  80

Lys Ala Glu Asp Leu Gln Pro Ala Val Asp Asp Ser Val Glu His Ser
                85                  90                  95

Ser Ser Glu Val Gly Glu Lys Val Ser Glu Thr Ser Lys Glu Glu Asn
            100                 105                 110

Thr Pro Glu Val Lys Ala Glu Asp Leu Gln Pro Ala Val Asp Gly Ser
        115                 120                 125

Ile Glu His Ser Ser Ser Glu Val Gly Glu Lys Val Ser Lys Thr Ser
    130                 135                 140

Lys Glu Glu Ser Thr Pro Glu Val Lys Ala Glu Asp Leu Gln Pro Ala
145                 150                 155                 160

Val Asp Asp Ser Val Glu His Ser Ser Ser Glu Val Gly Glu Lys Val
                165                 170                 175

Ser Glu Thr Ser Lys Glu Glu Asn Thr Pro Glu Val Lys Ala Glu Asp
            180                 185                 190

Leu Gln Pro Ala Val Asp Gly Ser Val Glu His Ser Ser Ser Glu Val
        195                 200                 205

Gly Glu Lys Val Ser Lys Thr Ser Lys Glu Glu Ser Thr Pro Glu Val
    210                 215                 220

Lys Ala Glu Asp Leu Gln Pro Ala Val Asp Asp Ser Val Glu His Ser
225                 230                 235                 240

Ser Ser Glu Val Gly Glu Lys Val Ser Glu Thr Ser Lys Glu Glu Asn
                245                 250                 255

Thr Pro Glu Val Arg Ala Glu Asp Leu Gln Pro Ala Val Asp Gly Ser
```

```
                    260                 265                 270
Val Glu His Ser Ser Glu Val Gly Glu Lys Val Ser Glu Thr Ser
                275                 280                 285
Lys Glu Glu Ser Thr Pro Glu Val Lys Ala Glu Asp Leu Gln Pro Ala
            290                 295                 300
Val Asp Ser Ser Ile Glu His Ser Ser Glu Val Gly Lys Lys Val
305                 310                 315                 320
Ser Glu Thr Ser Lys Glu Glu Ser Thr Pro Glu Val Lys Ala Glu Asp
                325                 330                 335
Leu Gln Pro Ala Val Asp Gly Ser Val Glu His Ser Ser Glu Val
                340                 345                 350
Gly Glu Lys Val Ser Glu Thr Ser Lys Glu Glu Asn Thr Pro Glu Val
                355                 360                 365
Lys Ala Glu Asp Leu Gln Pro Ala Val Asp Gly Ser Val Glu His Ser
            370                 375                 380
Ser Glu Val Gly Lys Val Ser Glu Thr Ser Lys Glu Glu Asn
385                 390                 395                 400
Thr Pro Glu Val Lys Ala Glu Asp Leu Gln Pro Ala Val Asp Gly Ser
                405                 410                 415
Val Glu His Ser Ser Glu Val Gly Glu Lys Val Ser Glu Thr Ser
                420                 425                 430
Lys Glu Glu Ser Thr Pro Glu Val Lys Ala Glu Asp Leu Gln Pro Ala
            435                 440                 445
Val Asp Asp Ser Val Glu His Ser Ser Glu Val Gly Glu Lys Val
                450                 455                 460
Ser Glu Thr Ser Lys Glu Ser Thr Pro Glu Val Lys Ala Glu Asp
465                 470                 475                 480
Leu Gln Pro Ala Val Asp Gly Ser Val Glu His Ser Ser Glu Val
                485                 490                 495
Gly Glu Lys Val Ser Glu Thr Ser Lys Glu Glu Ser Thr Pro Glu Val
                500                 505                 510
Lys Ala Glu
        515

<210> SEQ ID NO 17
<211> LENGTH: 36
<212> TYPE: PRT
<213> ORGANISM: Ehrlichia canis
<220> FEATURE:
<221> NAME/KEY: MISC_FEATURE
<222> LOCATION: (4)..(4)
<223> OTHER INFORMATION: X stands for any amino acid
<220> FEATURE:
<221> NAME/KEY: MISC_FEATURE
<222> LOCATION: (9)..(9)
<223> OTHER INFORMATION: X stands for any amino acid
<220> FEATURE:
<221> NAME/KEY: MISC_FEATURE
<222> LOCATION: (19)..(19)
<223> OTHER INFORMATION: X stands for any amino acid
<220> FEATURE:
<221> NAME/KEY: MISC_FEATURE
<222> LOCATION: (21)..(21)
<223> OTHER INFORMATION: X stands for any amino acid
<220> FEATURE:
<221> NAME/KEY: MISC_FEATURE
<222> LOCATION: (30)..(30)
<223> OTHER INFORMATION: X stands for any amino acid
<220> FEATURE:
<221> NAME/KEY: MISC_FEATURE
<222> LOCATION: (34)..(34)
<223> OTHER INFORMATION: X stands for any amino acid
```

-continued

```
<400> SEQUENCE: 17

Lys Glu Glu Xaa Thr Pro Glu Val Xaa Ala Glu Asp Leu Gln Pro Ala
1               5                   10                  15

Val Asp Xaa Ser Xaa Glu His Ser Ser Ser Glu Val Gly Xaa Lys Val
            20              25                  30

Ser Xaa Thr Ser
        35
```

*EHRLICHIA CANIS* DIVA (DIFFERENTIATE INFECTED FROM VACCINATED ANIMALS)

PRIORITY

This application is a divisional of U.S. application Ser. No. 11/397,222, filed Apr. 4, 2006 (now allowed), which claims the benefit of U.S. Appl. No. 60/668,205, filed on Apr. 4, 2005, all of which are incorporated herein by reference in their entirety.

SEQUENCE LISTING

This document incorporates by reference an electronic sequence listing text file, which was electronically submitted along with this document. The text file is named "04_947_A-DIV.seq list.txt," is 76,608 bytes, and was created on Nov. 30, 2010.

BACKGROUND OF THE INVENTION

The *Ehrilichia* are obligate intracellular pathogens that infect circulating white blood cells in mammalian hosts. *Ehrlichia canis* can infect canines and humans and cause canine monocytic ehrlichiosis (CME) and human monocytic ehrlichiosis (HME), respectively. The canine disease is characterized by fever, lymphadenopathy, weight loss, and pancytopenia. In humans the disease is characterized by fever, headache, mylagia, and leukopenia. Early detection and treatment are important for treating both canine and human ehrlichiosis.

SUMMARY OF THE INVENTION

In one embodiment the invention provides a method for determining whether an animal is infected with *Ehrlichia canis*, or is either not infected or is vaccinated with an *E. canis* vaccine. The method comprises contacting a biological sample from the animal with a first purified *E. canis* polypeptide that is not an element of the *E. canis* vaccine; and detecting whether an antibody in the sample specifically binds to the first purified *E. canis* polypeptide. If an antibody in the sample specifically binds to the first purified *E. canis* polypeptide, then the animal is infected with *E. canis* and if an antibody does not specifically bind to the purified *E. canis* polypeptide, then the animal is either vaccinated or is not infected. The first purified *E. canis* polypeptide can comprise SEQ ID NOs:2, 4, 6, 8, 10, 12, 14, 15, 16, 17 or a combination thereof. The *E. canis* vaccine can comprise at least one *E. canis* p28-1, p28-2, p28-3, p28-4, p28-5, p28-6, p28-7, p28-8, p28-9, proA, ProB, mmpA, cytochrome oxidase, p43, p153 polypeptide, or a combination thereof. The *E. canis* vaccine can comprise a vector encoding at least one *E. canis* p28-1, p28-2, p28-3, p28-4, p28-5, p28-6, p28-'7, p28-8, p28-9, proA, ProB, mmpA, cytochrome oxidase, p43, p153 polypeptide, or a combination thereof.

The method can further comprise detecting whether an antibody in the sample specifically binds to a second purified *E. canis* polypeptide that is an element of an *E. canis* vaccine, and determining that the animal has been vaccinated for *E. canis* by detecting that an antibody in the sample specifically binds to the second purified *E. canis* polypeptide, or determining that the animal has not been vaccinated for *E. canis* and has not been infected by *E. canis* by detecting that no antibody in the sample specifically binds to the second purified *E. canis* polypeptide.

Another embodiment of the invention provides a method of distinguishing between animals that have been infected with *E. canis* and animals that have not been infected or have been vaccinated with an *E. canis* vaccine. The method comprises contacting a biological sample from an animal with a first purified *E. canis* polypeptide that does not specifically bind to antibodies that are a component of the animal's immune response to an *E. canis* vaccine, detecting whether an antibody in the sample specifically binds to the first purified *E. canis* polypeptide, and determining that the animal is infected by correlating a positive result in the detecting step to a natural infection and determining that the animal has been vaccinated or is not infected by correlating a negative result to a vaccination or no infection. The first purified *E. canis* polypeptide can comprise SEQ ID NOs: 2, 4, 6, 8, 10, 12, 14, 15, 16, 17 or combinations thereof. The method can further comprise detecting whether an antibody in the sample specifically binds to a second purified *E. canis* polypeptide that specifically binds an antibody that is a component of the animal's immune response to the vaccine, thereby determining whether the animal has been vaccinated.

Still another embodiment of the invention provides a method of determining whether an animal is either not infected or has been vaccinated against *E. canis* with an *E. canis* vaccine, or is infected with *E. canis* comprising determining the animal's immune response to a first purified polypeptide derived from *E. canis* that is not an element of an *E. canis* vaccine. The first *E. canis* polypeptide can comprise SEQ ID NOs: 2, 4, 6, 8, 10, 12, 14, 15, 16, 17 or combinations thereof. The method can further comprise determining, in those animals that do not have an immune response to the first purified polypeptide, whether the animal has been vaccinated by determining the animal's immune response to a second purified polypeptide that is an element of the *E. canis* vaccine.

Even another embodiment of the invention provides a method for determining the vaccination or infection status of an animal for *E. canis*. The method comprises contacting a biological sample from the animal with a reagent comprising a first purified *E. canis* polypeptide that is not an element of an *E. canis* vaccine and detecting whether the first purified *E. canis* polypeptide specifically binds to an antibody in the biological sample. If the first purified *E. canis* polypeptide specifically binds to an antibody in the sample, then the animal is infected with *E. canis* and, if the first purified *E. canis* polypeptide does not specifically bind to an antibody in the sample, then the animal is either not infected with *E. canis* or has been vaccinated with a vaccine that does not comprise the first purified *E. canis* polypeptide. The first purified *E. canis* polypeptide can comprise SEQ ID NOs: 2, 4, 6, 8, 10, 12, 14, 15, 16, 17 or combinations thereof. The method can further comprise, detecting whether an antibody in the sample specifically binds to a second purified *E. canis* polypeptide that specifically binds an antibody that is a component of the animal's immune response to the *E. canis* vaccine, thereby determining whether the animal has been vaccinated.

Another embodiment of the invention provides a method of determining whether an animal is infected with *E. canis*, is vaccinated with an *E. canis* vaccine, or is not infected and not vaccinated. The method comprises contacting a biological sample from the animal with a first purified *E. canis* polypeptide that is not an element of the *E. canis* vaccine, contacting the biological sample with a second purified *E. canis* polypeptide that is an element of the *E. canis* vaccine; and detecting whether antibodies in the sample specifically bind to the first and the second purified *E. canis* polypeptides. If antibodies in the sample specifically bind to both the first and second purified *E. canis* polypeptides, then the animal is infected with *E. canis*, and if an antibody in the sample specifically binds to the second purified *E. canis* polypeptide but not the first purified *E. canis* polypeptide, then the animal has been vaccinated but is not infected and wherein, and if an antibody does not specifically bind to either polypeptide, then the animal is not infected and not vaccinated. The first purified *E. canis* polypeptide can comprise SEQ ID NOs: 2, 4, 6, 8, 10, 12, 14, 15, 16, 17 or combinations thereof.

Yet another embodiment of the invention provides a method of determining an animal's vaccination and infection status for *E. canis*. The method comprises contacting a biological sample from an animal with a first purified polypeptide that does not specifically bind to antibodies that are a component of the animal's immune response to an *E. canis* vaccine and a second polypeptide that specifically binds to an antibody that is a component of the animal's immune response to an *E. canis* vaccine; detecting whether antibodies in the sample specifically bind to the first and second purified polypeptides; determining that the animal is infected by detecting the specific binding of antibodies in the sample to both the first and second purified polypeptides, determining that that the animal is vaccinated and not infected by detecting the specific binding of an antibody to the second purified polypeptide but not the first purified polypeptide, and determining that the animal is not vaccinated and not infected by detecting the absence of specific binding to the first and second purified *E. canis* polypeptides. The first *E. canis* polypeptide can comprise SEQ ID NOs: 2, 4, 6, 8, 10, 12, 14, 15, 16, 17 or combinations thereof.

Even another embodiment of the invention provides a method for determining the presence or absence of an antibody or fragment thereof, in a test sample, wherein the antibody or fragment thereof specifically binds to a purified polypeptide comprising SEQ ID NOs: 2, 4, 6, 8, 10, 12, 14, 15, 16, or 17. The method comprises contacting the test sample with a purified polypeptide comprising SEQ ID NOs: 2, 4, 6, 8, 10, 12, 14, 15, 16, or 17 under conditions suitable for specific binding of the purified polypeptide to the antibody or fragment thereof, and detecting the presence or absence of specific binding. The presence of specific binding indicates the presence of the antibody or fragment thereof. The absence of specific binding indicates the absence the antibody or fragment thereof. The method can further comprise detecting the amount of specific binding. The test sample can be serum, blood, or saliva. The purified polypeptide can be immobilized to a solid support. The purified polypeptide can be labeled. The detection can be by radioimmunoassay, enzyme-linked immunosorbent assay, immunohistochemical, or immunoenzyme-assay.

Yet another embodiment of the invention provides a method for determining the presence or absence of a polypeptide comprising SEQ ID NOs: 2, 4, 6, 8, 10, 12, 14, 15, 16, 17 in a test sample. The method comprises contacting the test sample with an antibody or fragment thereof that specifically binds a purified polypeptide consisting of SEQ ID NOs: 2, 4, 6, 8, 10, 12, 14, 15, 16, 17 under conditions suitable for specific binding of the polypeptide to the antibody or fragment thereof, and detecting the presence or absence of specific binding. The presence of specific binding indicates the presence of the polypeptide, and the absence of specific binding indicates that the absence the polypeptide. The method can further comprise detecting the amount of specific binding. The test sample can be serum, blood, or saliva. The antibody or fragment thereof can be immobilized to a solid support. The antibody or fragment thereof can be labeled. The detection can be by radioimmunoassay, enzyme-linked immunosorbent assay, immunohistochemical assay or immunoenzyme-assay.

Another embodiment of the invention provides a composition comprising one or more purified polypeptides consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:15, SEQ ID NO:16, SEQ ID NO:17 or combinations thereof and a polynucleotide encoding the one or more purified polypeptides.

The purified polypeptide can be in a multimeric form. The purified polypeptide can be linked to a heterologous protein (an amino acid sequence not normally associated with the purified polypeptide in nature) an indicator reagent, an amino acid spacer, an amino acid linker, a signal sequence, a stop transfer sequence, a transmembrane domain, a protein purification ligand, or a combination thereof.

Even another embodiment of the invention provides a fusion protein comprising one or more polypeptides consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:15, SEQ ID NO:16, SEQ ID NO:17 or a combination thereof.

Another embodiment of the invention provides a method of generating an immune response in an animal comprising administering one or more purified polypeptides comprising SEQ ID NOs:2, 4, 6, 8, 10, 15, 16, 17, or a combination thereof to the animal.

Yet another embodiment of the invention provides a method for the prophylaxis, treatment, or amelioration of an *Ehrlichia canis* infection in an animal. The method comprises administering (1) one or more purified polypeptides comprising SEQ ID NOs:2, 4, 6, 8, 10, 15, 16, 17, or a combination thereof;

one or more nucleic acids encoding one or more purified polypeptides comprising SEQ ID NOs:2, 4, 6, 8, 10, 15, 16, 17, or a combination thereof.

Therefore, the invention provides *Ehrlichia canis* antigens that can be used to differentiate *E. canis* naturally-infected animals from animals that have been challenged with *E. canis*, e.g., vaccinated against *E. canis*. The invention also provides compositions and methods for determining the presence of *E. canis* antigens and antibodies and for the treatment, amelioration, and prevention of *E. canis* infection.

BRIEF DESCRIPTION OF THE DRAWINGS

FIG. 8 shows the repeated sequence in SEQ ID NO: 15.

FIG. 9A shows SEQ ID NO:16.

FIG. 9B shows SEQ ID NO:17.

DETAILED DESCRIPTION OF THE INVENTION

Figure 1:
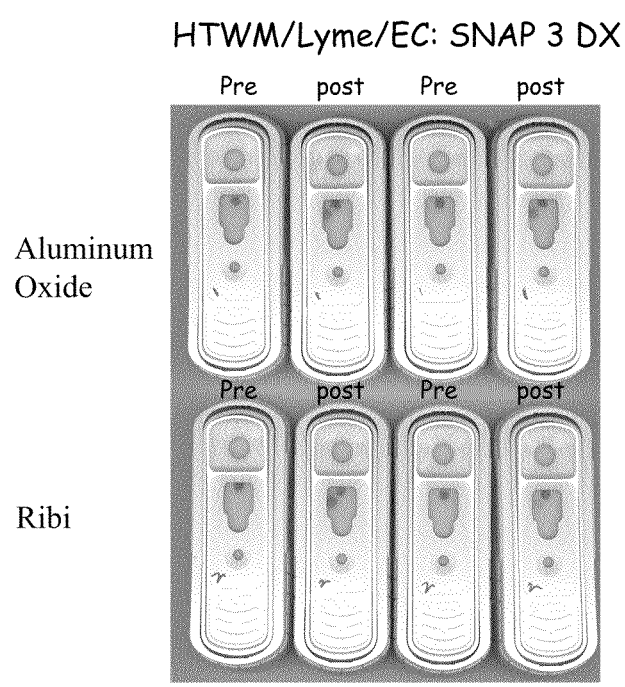
FIG. 1 shows SNAP® 3Dx® reversible flow chromatographic assay evaluation of laboratory beagles. The SNAP® reversible flow chromatographic assay device was used as described by manufacturer. "Pre" sample is from day 0. "Post" sample is from day 42. The *E. canis* positive spot became positive in all 4 dogs for the day 42 sample. Similar results were observed for the day 70 sample.

*Ehrlichia canis* antigens that can be used to differentiate *E. canis* naturally-infected animals from animals that have been challenged with *E. canis*, e.g., vaccinated against *E. canis*, are disclosed.

Before describing the present invention in detail, a number of terms will be defined. As used herein, the singular forms "a," "an", and "the" include plural referents unless the context clearly dictates otherwise.

As used herein, the term "polypeptide" refers to a compound of a single chain or a complex of two or more chains of amino acid residues linked by peptide bonds. The chain(s) may be of any length and can comprise a fusion protein. Although "protein" is often used in reference to relatively large polypeptides, and "peptide" is often used in reference to small polypeptides, usage of these terms in the art overlaps and varies. The term "polypeptide" as used herein thus refers interchangeably to peptides, polypeptides, proteins, or fusion proteins unless otherwise noted. The term "amino acid" refers to a monomeric unit of a peptide, polypeptide or protein.

As used herein, "antigen" as used herein refers to a molecule against which a subject can initiate a humoral and/or cellular immune response. Antigens can be any type of biologic molecule including, for example, simple intermediary metabolites, sugars, lipids, and hormones as well as macromolecules such as complex carbohydrates, phospholipids, nucleic acids and proteins. In the compositions and methods of the invention, it is preferred that the antigen is a polypeptide, e.g., one comprising at least about six or more amino acids.

As used herein, a "derivative" of an *E. canis* antigen polypeptide, or an antigen or polypeptide that is "derived from" an *E. canis* antigen or polypeptide, refers to a antigen or polypeptide in which the native form has been purified, modified or altered. Such modifications include, but are not limited to: amino acid substitutions, modifications, additions or deletions; alterations in the pattern of lipidation, glycosylation or phosphorylation; reactions of free amino, carboxyl, or hydroxyl side groups of the amino acid residues present in the polypeptide with other organic and non-organic molecules; and other modifications, any of which may result in changes in primary, secondary or tertiary structure.

A "biological sample" is any sample from an animal that is expected to contain immunoglobulins. Generally, these samples are whole blood and blood components, but in some circumstances may include saliva, urine, tears, other bodily fluids, tissue extracts or cellular extracts.

An "infection," such as in an *E. canis* infection, means that an animal has been exposed to *E. canis*, regardless of whether the animal exhibits clinical symptoms of *E. canis*. A natural infection refers to an exposure that occurs as a result of one of the natural transmission methods for *E. canis*, such as transmission by ticks. An infection does not include an exposure to *E. canis* through vaccination.

A "polypeptide or antigen that is not an element of an *E. canis* vaccine" is any *E. canis* polypeptide or antigen that is not present in, or is not an immunogenically active portion of, a particular *E. canis* vaccine or vaccines. Elements of the vaccine(s) can be portions of a subunit vaccine that includes less than the entire bacterium; these portions can be chemically synthesized or expressed recombinantly before becoming part of the vaccine, and these portions can be encoded by one or more vectors that express an immunogenic composition in vivo.

An "antibody that is a component of an animal's immune response to an *E. canis* vaccine" refers to an antibody that is elicited as the result of a vaccination with an *E. canis* vaccine. These antibodies can be identical to or similar to antibodies elicited as the result of a natural *E. canis* infection. These antibodies will be maintained at a sufficient titer and so as to provide a protective and neutralizing effect against the bacteria. A successful vaccination produces a measurable level of the antibody (or antibodies) that is elicited by a component of the *E. canis* vaccine. Examples of *E. canis* antigens that elicit antibodies that can be a component of an animal's immune response to an *E. canis* vaccine are p28-1, p28-2, p28-3, p28-4, p28-5, p28-6, p28-7, p28-8, p28-9 (see U.S. Pat. Nos. 6,660,269; 6,458,942; 6,403,780; 6,392,023), proA, ProB, mmpA, cytochrome oxidase (see U.S. Pat. Publ. 20040170972), p43 (see U.S. Pat. No. 6,355,777), which is the N-terminal portion of p153, a glycoprotein (see U.S. Pat. Publ. 2004/0121433), and p153.

An immune response is the development in an organism of a cellular and/or antibody mediated immune response to an antigen such as a polypeptide. Usually such a response includes but is not limited to one or more of the following: production of antibodies, B cells, helper T cells, suppressor T cells, and/or cytotoxic T cells. An immune response can be detected using any of several assays known to those with skill in the art.

Polypeptides of the Invention

Biological samples from animals that have been vaccinated against *E. canis* have the potential for producing a positive result in a test for *E. canis* infection due to the presence of antibodies produced in response to the vaccine. In one aspect, the invention provides a method of distinguishing between animals that have been infected with *E. canis*, animals that have not been infected with *E. canis*, and animals that have been vaccinated against *E. canis*. Methods include contacting a biological sample from the animal with an antigen derived from *E. canis* that does not specifically bind to an antibody that is a component of the animal's antibody response to a particular *E. canis* vaccine.

The development of *E. canis* antibodies in an animal against a vaccine is dependent upon the particular vaccine used to vaccinate the animal. The difference in the immune response between animals that are vaccinated against *E. canis* and animals that are naturally or experimentally infected with *E. canis* provides a means for determining whether an animal has been vaccinated or is naturally or experimentally infected. Therefore, using the methods of the invention, animals that have been infected with *E. canis* can be distinguished from animals that have not been infected with *E. canis* or have been vaccinated against *E. canis*. Antigens of the invention, their immunodominant regions, and epitopes can be used in the methods of the invention. These compositions can be referred to as *E. canis* DIVA antigens (Differentiate Infected from Vaccinated Animals). An *E. canis* DIVA antigen induces an immune response, e.g., the production of specific antibodies, in an animal that is different from the immune response induced in the animal by a particular *E. canis* vaccine.

Accordingly, the detection of the binding between an *E. canis* DIVA antigen and an antibody that is not a component of an animal's immune response to a particular vaccine can indicate a natural infection. The absence of such binding can indicate vaccination or no infection. In addition, a second, separate antigen, such as an *E. canis* antigen that specifically binds an antibody that is a component of animal's immune response to a particular *E. canis* vaccine, can be used to detect antibodies produced in response to vaccination. The detection of neither antibody indicates no infection and no vaccination. As such, various combinations of separate capture reagents can lead to a determination of the vaccination and/or infection status of the test subject.

In one aspect, a method of the invention includes contacting a biological sample from an animal with an antigen that is a part of the native *E. canis* bacteria, but is not an element of a particular *E. canis* vaccine. An animal is any mammal that is likely to be vaccinated against *E. canis* and, in particular, canines. In addition, humans may be vaccinated against *E. canis*. In another aspect, the invention includes a method of determining whether an animal has not been infected by *E. canis* and has not been vaccinated against *E. canis*. A biological sample from an animal is analyzed to detect the presence or absence of antibodies specific for an *E. canis* DIVA antigen, and the presence or absence of antibodies specific for a particular *E. canis* vaccine. It is then determined that the animal has not been infected and has not been or vaccinated by determining the absence of such antibodies.

In one aspect of the invention, a DIVA antigen is not an element of an *E. canis* vaccine. The vaccination or infection status of an animal can be determined by detecting whether antibodies in the sample bind to one or more antigens used in the vaccine. If antibodies in the sample bind to one or more of the antigens, the animal is either vaccinated or infected. If no antibody binds the DIVA polypeptide, then it can be determined that the animal has been vaccinated. If no binding is detected for either antigen, then it can be determined that the animal is not infected and not vaccinated.

A polypeptide of the invention can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure.

Purified polypeptides of the invention can either be full-length polypeptides or fragments of polypeptides. For example, fragments of polypeptides of the invention can comprise about 6, 10, 20, 30, 40, 50, 60, 70, 80, 90, 100, 250, 500, 750 contiguous amino acids or more of polypeptides of the invention. Examples of polypeptides of the invention include those shown in SEQ ID NOs:2, 4, 6, 8, 10, 12, 14, 15, 16, or 17. Variant polypeptides are at least about 80, or about 90, 96, 98, or 99% identical to the polypeptide sequences shown in SEQ ID NOs: 2, 4, 6, 8, 10, 12, 14, 15, 16, or 17 and are also polypeptides of the invention. Variant polypeptides have one or more conservative amino acid variations or other minor modifications and retain biological activity, i.e., are biologically functional equivalents. A biologically active equivalent has substantially equivalent function when compared to the corresponding wild-type polypeptide.

Percent sequence identity has an art recognized meaning and there are a number of methods to measure identity between two polypeptide or polynucleotide sequences. See, e.g., Lesk, Ed., *Computational Molecular Biology*, Oxford University Press, New York, (1988); Smith, Ed., *Biocomputing: Informatics And Genome Projects*, Academic Press, New York, (1993); Griffin & Griffin, Eds., *Computer Analysis Of Sequence Data, Part I*, Humana Press, New Jersey, (1994); von Heinje, *Sequence Analysis In Molecular Biology*, Academic Press, (1987); and Gribskov & Devereux, Eds., *Sequence Analysis Primer*, M Stockton Press, New York, (1991). Methods for aligning polynucleotides or polypeptides are codified in computer programs, including the GCG program package (Devereux et al., *Nuc. Acids Res.* 12:387 (1984)), BLASTP, BLASTN, FASTA (Atschul et al., *J. Molec. Biol.* 215:403 (1990)), and Bestfit program (Wisconsin Sequence Analysis Package, Version 8 for Unix, Genetics Computer Group, University Research Park, 575 Science Drive, Madison, Wis. 53711) which uses the local homology algorithm of Smith and Waterman (*Adv. App. Math.,* 2:482-489 (1981)). For example, the computer program ALIGN which employs the FASTA algorithm can be used, with an affine gap search with a gap open penalty of −12 and a gap extension penalty of −2.

When using any of the sequence alignment programs to determine whether a particular sequence is, for instance, about 95% identical to a reference sequence, the parameters are set such that the percentage of identity is calculated over the full length of the reference polynucleotide and that gaps in identity of up to 5% of the total number of nucleotides in the reference polynucleotide are allowed.

Variants can generally be identified by modifying one of the polypeptide sequences of the invention, and evaluating the properties of the modified polypeptide to determine if it is a biological equivalent. A variant is a biological equivalent if it reacts substantially the same as a polypeptide of the invention in an assay such as an immunohistochemical assay, an enzyme-linked immunosorbent Assay (ELISA), a radioimmunoassay (RIA), immunoenzyme assay or a western blot assay, e.g. has 90-110% of the activity of the original polypeptide. In one embodiment, the assay is a competition assay wherein the biologically equivalent polypeptide is capable of reducing binding of the polypeptide of the invention to a corresponding reactive antigen or antibody by about 80, 95, 99, or 100%. An antibody that specifically binds a corresponding wild-type polypeptide also specifically binds the variant polypeptide. Variant polypeptides of the invention can comprise about 1, 2, 3, 4, 5, or 6 conservative amino acid substitutions.

A conservative substitution is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A polypeptide of the invention can further comprise a signal (or leader) sequence that co-translationally or post-translationally directs transfer of the protein. The polypeptide can also comprise a linker or other sequence for ease of synthesis, purification or identification of the polypeptide (e.g., poly-His), or to enhance binding of the polypeptide to a solid support. For example, a polypeptide can be conjugated to an immunoglobulin Fc region or bovine serum albumin.

A polypeptide can be covalently or non-covalently linked to an amino acid sequence to which the polypeptide is not normally associated with in nature. Additionally, a polypeptide can be covalently or non-covalently linked to compounds or molecules other than amino acids. For example, a polypeptide can be linked to an indicator reagent, an amino acid spacer, an amino acid linker, a signal sequence, a stop transfer sequence, a transmembrane domain, a protein purification ligand, or a combination thereof. In one embodiment of the invention a protein purification ligand can be one or more C amino acid residues at, for example, the amino terminus or carboxy terminus of a polypeptide of the invention. An amino acid spacer is a sequence of amino acids that are not usually associated with a polypeptide of the invention in nature. An amino acid spacer can comprise about 1, 5, 10, 20, 100, or 1,000 amino acids.

If desired, a polypeptide can be a fusion protein, which can also contain other amino acid sequences, such as amino acid linkers, amino acid spacers, signal sequences, TMR stop transfer sequences, transmembrane domains, as well as ligands useful in protein purification, such as glutathione-S-transferase, histidine tag, and staphylococcal protein A, or combinations thereof. More than one polypeptide of the invention can be present in a fusion protein. Fragments of polypeptides of the invention can be present in a fusion protein of the invention. A fusion protein of the invention can comprise one or more polypeptides shown in SEQ ID NO: 2, 4, 6, 8, 10, 12, 14, 15, 16, or 17, fragments thereof, or combinations thereof.

Polypeptides of the invention can be in a multimeric form. That is, a polypeptide can comprise one or more copies of SEQ ID NOs: 2, 4, 6, 8, 10, 12, 14, 15, 16, 17 or a combination thereof. A multimeric polypeptide can be a multiple antigen peptide (MAP). See e.g., Tam, J. Immunol. Methods, 196:17-32 (1996).

Polypeptides of the invention can comprise an antigen that is recognized by an antibody reactive against *E. canis*. The antigen can comprise one or more epitopes (i.e., antigenic determinants). An epitope can be a linear epitope, sequential epitope or a conformational epitope. Epitopes within a polypeptide of the invention can be identified by several methods. See, e.g., U.S. Pat. No. 4,554,101; Jameson & Wolf, *CABIOS* 4:181-186 (1988). For example, a polypeptide of the invention can be isolated and screened. A series of short peptides, which together span an entire polypeptide sequence, can be prepared by proteolytic cleavage. By starting with, for example, 100-mer polypeptide fragments, each fragment can be tested for the presence of epitopes recognized in an ELISA. For example, in an ELISA assay an *E. canis* polypeptide, such as a 100-mer polypeptide fragment, is attached to a solid support, such as the wells of a plastic multi-well plate. A population of antibodies are labeled, added to the solid support and allowed to bind to the unlabeled antigen, under conditions where non-specific absorption is blocked, and any unbound antibody and other proteins are washed away. Antibody binding is detected by, for example, a reaction that converts a colorless substrate into a colored reaction product. Progressively smaller and overlapping fragments can then be tested from an identified 100-mer to map the epitope of interest.

In one embodiment of the invention, a DIVA antigen comprises an immunodominant epitope or region. That is, an epitope or region that more frequently elicits and binds to antibodies in a population thereof when compared with other epitopes. An antigen can have one or more immunodominant epitopes. Immunodominant epitopes can be mapped on, for example, a polypeptide after the polypeptide has been administered to an animal or prior to such administration. See e.g., U.S. Pat. Publ. 2004/0209324.

A polypeptide of the invention can be produced recombinantly. A polynucleotide encoding a polypeptide of the invention can be introduced into a recombinant expression vector, which can be expressed in a suitable expression host cell system using techniques well known in the art. A variety of bacterial, yeast, plant, mammalian, and insect expression systems are available in the art and any such expression system can be used. Optionally, a polynucleotide encoding a polypeptide can be translated in a cell-free translation system. A polypeptide can also be chemically synthesized or obtained from *E. canis* cells.

An immunogenic polypeptide of the invention can comprise an amino acid sequence shown in SEQ ID NOs: 2, 4, 6, 8, 10, 12, 14, 15, 16, or 17. An immunogenic polypeptide can elicit antibodies or other immune responses (e.g., T-cell responses of the immune system) that recognize epitopes of polypeptides having SEQ ID NOs: 2, 4, 6, 8, 10, 12, 14, 15, 16, or 17. An immunogenic polypeptide of the invention can also be a fragment of a polypeptide that has an amino acid sequence shown in SEQ ID NOs: 2, 4, 6, 8, 10, 12, 14, 15, 16, 17. An immunogenic polypeptide fragment of the invention can be about 6, 10, 20, 30, 40, 50, 60, 70, 80, 90, 100, 250, 500, 750 amino acids in length.

Antibodies specific for *E. canis* can be detected in biological fluids or tissues by any method known in the art. The simplest methods generally are immunoassay methods. One such method is a competition-based method wherein serum samples are preincubated with an *E. canis* antigen that is not an element of an *E. canis* vaccine (e.g., an *E. canis* DIVA antigen), and then added to a solid phase, such a microtiter plate, having an immobilized monoclonal antibody specific for the *E. canis* DIVA antigen. Antibodies specific for the *E. canis* DIVA antigen in the sample will prevent the *E. canis* DIVA antigen from binding to the immobilized antibody. Detection of any binding of the *E. canis* DIVA antigen to the immobilized antibody can be determined by adding a second binding partner for the *E. canis* antigen, either directly labeled or capable of becoming labeled through binding to another binding partner having a label. A positive sample, i.e. a sample having antibodies specific for an *E. canis* DIVA antigen, is associated with a decrease in signal from the label.

In one particular embodiment, antibodies to an *E. canis* DIVA antigen in a biological sample can be detected by contacting the sample with an *E. canis* DIVA antigen and adding the sample to microtiter plate coated with an anti-DIVA antigen monoclonal antibody. Binding of the DIVA antigen to the microtiter plate can be detected by adding a rabbit polyclonal antibody against the DIVA antigen and adding an HRP-conjugated donkey anti-rabbit polyclonal antibody. Antibodies in the sample will prevent the binding of the DIVA antigen to the immobilized antibody, thereby causing a decrease in signal.

Another method for detecting antibodies specific for an *E. canis* DIVA antigen is a sandwich assay where a biological sample suspected of containing an antibody specific for an *E.*

*canis* DIVA antigen is contacted with an immobilized *E. canis* DIVA antigen to form an immunological complex. The presence of an antibody specific for an *E. canis* DIVA antigen is determined by the detection of the binding of a labeled binding partner for the *E. canis* antibody, such as a second antibody.

In one aspect of the invention, *E. canis* DIVA antigens can be immobilized on a suitable solid support. A biological sample is brought into contact with the *E. canis* DIVA antigen, to which the anti-*E. canis* antibodies bind, if such antibodies are present in the sample. The binding can be detected by any suitable means, e.g., enzymes, radionuclides, particulates or fluorescent labels. In a suitable embodiment, the detection reagent can be associated with a protein that is the same or similar to that which is used to capture anti-*E. canis* antibodies (if present). In one particular embodiment, antibodies to *E. canis* can be detected by immobilizing an *E. canis* antigen on a solid support. Biological samples can be contacted with the solid support and, following the removal of unbound sample, binding of the *E. canis* antibodies to the antigen can be accomplished with, for example, a labeled IgG antibody.

DIVA antigens of the invention can also comprise mimitopes of DIVA antigens of the invention. A mimitope is a random peptide epitope that mimics a natural antigenic epitope during epitope presentation. Random peptide epitopes can be identified by generating or selecting a library of random peptide epitopes. The library is contacted with an antibody. Mimitopes are identified that are specifically immunoreactive with the antibody. Random peptide libraries can, for example, be displayed on phage or generated as combinatorial libraries.

*E. canis* DIVA antigens, e.g., polypeptides, can be natural, i.e., isolated from a natural source, or can be synthetic (i.e., chemically synthesized or recombinantly produced using genetic engineering techniques). Natural proteins can be isolated from the whole bacterium by conventional techniques, such as affinity chromatography. Polyclonal or monoclonal antibodies can be used to prepare a suitable affinity column by well-known techniques.

Proteins that are immunologically cross-reactive with a natural *E. canis* protein can be chemically synthesized. For example, polypeptides having fewer than about 100 amino acids, more usually fewer than about 80 amino acids, and typically fewer than about 50 amino acids, can be synthesized by the well-known Merrifield solid-phase synthesis method where amino acids are sequentially added to a growing chain. Merrifield, 1963, J. Am. Chem. Soc., 85:2149-2156). Recombinant proteins can also be used. These proteins can be produced by expression in cultured cells of recombinant DNA molecules encoding a desired portion of the *E. canis* genome. The portion of the *E. canis* genome can itself be natural or synthetic, with natural genes obtainable from the isolated bacterium by conventional techniques.

*E. canis* Polynucleotides

Polynucleotides of the invention contain less than an entire microbial genome and can be single- or double-stranded nucleic acids. A polynucleotide can be RNA, DNA, cDNA, genomic DNA, chemically synthesized RNA or DNA or combinations thereof. The polynucleotides can be purified free of other components, such as proteins, lipids and other polynucleotides. For example, the polynucleotide can be 50%, 75%, 90%, 95%, 96%, 97%, 98%, 99%, or 100% purified. The polynucleotides of the invention encode the polypeptides described above. In one embodiment of the invention the polynucleotides encode polypeptides shown in SEQ ID NOs:2, 4, 6, 8, 10, 12, 14, 15, 16, 17 or combinations thereof. Polynucleotides of the invention include those shown in SEQ ID NO:1, 3, 5, 7, 9, 11, 13, or combinations thereof. Polynucleotides of the invention can comprise other nucleotide sequences, such as sequences coding for linkers, signal sequences, TMR stop transfer sequences, transmembrane domains, or ligands useful in protein purification such as glutathione-S-transferase, histidine tag, and staphylococcal protein A.

Polynucleotides of the invention can be isolated. An isolated polynucleotide is a polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. A nucleic acid molecule existing among hundreds to millions of other nucleic acid molecules within, for example, cDNA or genomic libraries, or gel slices containing a genomic DNA restriction digest are not to be considered an isolated polynucleotide. The complete nucleotide sequence for *E. canis* is available from, e.g., GenBank as accession number NCBI: NZ_AAEJ01000001.

Polynucleotides of the invention can also comprise fragments that encode immunogenic polypeptides. Polynucleotides of the invention can encode full-length polypeptides, polypeptide fragments, and variant or fusion polypeptides.

Degenerate nucleotide sequences encoding polypeptides of the invention, as well as homologous nucleotide sequences that are at least about 80, or about 90, 96, 98, or 99% identical to the polynucleotide sequences of the invention and the complements thereof are also polynucleotides of the invention. Percent sequence identity can be calculated as described in the "Polypeptides" section. Degenerate nucleotide sequences are polynucleotides that encode a polypeptide of the invention or fragments thereof, but differ in nucleic acid sequence from the wild-type polynucleotide sequence, due to the degeneracy of the genetic code. Complementary DNA (cDNA) molecules, species homologs, and variants of *E. canis* polynucleotides that encode biologically functional *E. canis* polypeptides also are *E. canis* polynucleotides. Polynucleotides of the invention can be isolated from nucleic acid sequences present in, for example, a biological sample, such as blood, serum, saliva, or tissue from an infected individual. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides of the invention can comprise coding sequences for naturally occurring polypeptides or can encode altered sequences that do not occur in nature. If desired, polynucleotides can be cloned into an expression vector comprising expression control elements, including for example, origins of replication, promoters, enhancers, or other regulatory elements that drive expression of the polynucleotides of the invention in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Minichromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

Methods for preparing polynucleotides operably linked to an expression control sequence and expressing them in a host cell are well-known in the art. See, e.g., U.S. Pat. No. 4,366,246. A polynucleotide of the invention is operably linked when it is positioned adjacent to or close to one or more expression control elements, which direct transcription and/or translation of the polynucleotide.

Polynucleotides of the invention can be used, for example, as probes or primers, for example PCR primers, to detect the presence of E. canis polynucleotides in a sample, such as a biological sample. The ability of such probes and primers to specifically hybridize to E. canis polynucleotide sequences will enable them to be of use in detecting the presence of complementary sequences in a given sample. Polynucleotide probes and primers of the invention can hybridize to complementary sequences in a sample such as a biological sample, including saliva, sputum, blood, urine, feces, cerebrospinal fluid, amniotic fluid, wound exudate, or tissue. Polynucleotides from the sample can be, for example, subjected to gel electrophoresis or other size separation techniques or can be immobilized without size separation. The polynucleotide probes or primers can be labeled. Suitable labels, and methods for labeling probes and primers are known in the art, and include, for example, radioactive labels incorporated by nick translation or by kinase, biotin labels, fluorescent labels, chemiluminescent labels, bioluminescent labels, metal chelator labels and enzyme labels. The polynucleotides from the sample are contacted with the probes or primers under hybridization conditions of suitable stringencies.

Depending on the application, varying conditions of hybridization can be used to achieve varying degrees of selectivity of the probe or primer towards the target sequence. For applications requiring high selectivity, relatively stringent conditions can be used, such as low salt and/or high temperature conditions, such as provided by a salt concentration of from about 0.02 M to about 0.15 M salt at temperatures of from about 50° C. to about 70° C. For applications requiring less selectivity, less stringent hybridization conditions can be used. For example, salt conditions from about 0.14 M to about 0.9M salt, at temperatures ranging from about 20° C. to about 55° C. The presence of a hybridized complex comprising the probe or primer and a complementary polynucleotide from the test sample indicates the presence of E. canis or an E. canis polynucleotide sequence in the sample.

Antibodies

Antibodies of the invention are antibody molecules that specifically and stably bind to an E. canis polypeptide of the invention or fragment thereof. An antibody of the invention can be a polyclonal antibody, a monoclonal antibody, a single chain antibody (scFv), or a fragment of an antibody. Fragments of antibodies are a portion of an intact antibody comprising the antigen binding site or variable region of an intact antibody, wherein the portion is free of the constant heavy chain domains of the Fc region of the intact antibody. Examples of antibody fragments include Fab, Fab', Fab'-SH, $F(ab')_2$ and $F_v$ fragments.

An antibody of the invention can be any antibody class, including for example, IgG, IgM, IgA, IgD and IgE. An antibody or fragment thereof binds to an epitope of a polypeptide of the invention. An antibody can be made in vivo in suitable laboratory animals or in vitro using recombinant DNA techniques. Means for preparing and characterizing antibodies are well know in the art. See, e.g., Dean, Methods Mol. Biol. 80:23-37 (1998); Dean, Methods Mol. Biol. 32:361-79 (1994); Baileg, Methods Mol. Biol. 32:381-88 (1994); Gullick, Methods Mol. Biol. 32:389-99 (1994); Drenckhahn et al. Methods Cell. Biol. 37:7-56 (1993); Morrison, Ann. Rev. Immunol. 10:239-65 (1992); Wright et al. Crit. Rev. Immunol. 12:125-68 (1992). For example, polyclonal antibodies can be produced by administering a polypeptide of the invention to an animal, such as a human or other primate, mouse, rat, rabbit, guinea pig, goat, pig, dog, cow, sheep, donkey, or horse. Serum from the immunized animal is collected and the antibodies are purified from the plasma by, for example, precipitation with ammonium sulfate, followed by chromatography, such as affinity chromatography. Techniques for producing and processing polyclonal antibodies are known in the art.

"Specifically binds" or "specific for" means that an antigen, e.g., a polypeptide, recognizes and binds to an antibody of the invention with greater affinity than to other, non-specific molecules. For example, an antibody raised against an antigen (e.g., a polypeptide) to which it binds more efficiently than to a non-specific protein can be described as specifically binding to the antigen. Binding specifically can be tested using, for example, an enzyme-linked immunosorbant assay (ELISA), a radioimmunoassay (RIA), or a western blot assay using methodology well known in the art.

Additionally, monoclonal antibodies directed against epitopes present on a antigen, e.g., a polypeptide of the invention, can also be readily produced. For example, normal B cells from a mammal, such as a mouse, which was immunized with a polypeptide of the invention can be fused with, for example, HAT-sensitive mouse myeloma cells to produce hybridomas. Hybridomas producing E. canis-specific antibodies can be identified using RIA or ELISA and isolated by cloning in semi-solid agar or by limiting dilution. Clones producing E. canis-specific antibodies are isolated by another round of screening. Monoclonal antibodies can be screened for specificity using standard techniques, for example, by binding a polypeptide of the invention to a microtiter plate and measuring binding of the monoclonal antibody by an ELISA assay. Techniques for producing and processing monoclonal antibodies are known in the art. See e.g., Kohler & Milstein, Nature, 256:495 (1975). Particular isotypes of a monoclonal antibody can be prepared directly, by selecting from the initial fusion, or prepared secondarily, from a parental hybridoma secreting a monoclonal antibody of a different isotype by using a sib selection technique to isolate class-switch variants. See Steplewski et al., P.N.A.S. U.S.A. 82:8653 1985; Spria et al., J. Immunolog. Meth. 74:307, 1984. Monoclonal antibodies of the invention can also be recombinant monoclonal antibodies. See, e.g., U.S. Pat. No. 4,474,893; U.S. Pat. No. 4,816,567. Antibodies of the invention can also be chemically constructed. See, e.g., U.S. Pat. No. 4,676,980.

Antibodies of the invention can be chimeric (see, e.g., U.S. Pat. No. 5,482,856), humanized (see, e.g., Jones et al., Nature 321:522 (1986); Reichmann et al., Nature 332:323 (1988); Presta, Curr. Op. Struct. Biol. 2:593 (1992)), or human antibodies. Human antibodies can be made by, for example, direct immortilization, phage display, transgenic mice, or a Trimera methodology, see e.g., Reisener et al., Trends Biotechnol. 16:242-246 (1998).

Antibodies that specifically bind E. canis antigens (e.g., E. canis polypeptides shown in SEQ ID NO:2, 4, 6, 8, 10, 12, 14, 15, 16, 17), are particularly useful for detecting the presence of E. canis or E. canis antigens in a sample, such as a serum, blood, urine or saliva sample from an *E. canis*-infected animal such as a human or dog. An immunoassay for *E. canis* or an *E. canis* antigen can utilize one antibody or several antibodies. An immunoassay for *E. canis* or an *E. canis* antigen can use, for example, a monoclonal antibody directed towards an *E. canis* epitope, a combination of monoclonal antibodies directed towards epitopes of one *E. canis* polypeptide, monoclonal antibodies directed towards epitopes of different *E. canis* polypeptides, polyclonal antibodies directed towards the same *E. canis* antigen, polyclonal antibodies directed towards different *E. canis* antigens, or a combination of monoclonal and polyclonal antibodies. Immunoassay protocols can be based upon, for example, competition, direct reaction, or sandwich type assays using, for example, labeled antibody. Antibodies of the invention can be labeled with any type of label known in the art, including, for example, fluorescent, chemiluminescent, radioactive, enzyme, colloidal metal, radioisotope and bioluminescent labels.

Antibodies of the invention or fragments thereof can be bound to a support and used to detect the presence of *E. canis* or an *E. canis* antigen, e.g., an *E. canis* DIVA antigen or *E. canis* non-DIVA antigen. Supports include, for example, glass, polystyrene, polypropylene, polyethylene, dextran, nylon, amylases, natural and modified celluloses, polyacrylamides, agaroses and magletite.

Antibodies of the invention can further be used to isolate *E. canis* organisms or *E. canis* antigens by immunoaffinity columns. The antibodies can be affixed to a solid support by, for example, adsorbtion or by covalent linkage so that the antibodies retain their immunoselective activity. Optionally, spacer groups can be included so that the antigen binding site of the antibody remains accessible. The immobilized antibodies can then be used to bind *E. canis* organisms or *E. canis* antigens from a sample, such as a biological sample including saliva, serum, sputum, blood, urine, feces, cerebrospinal fluid, amniotic fluid, wound exudate, or tissue. The bound *E. canis* organisms or *E. canis* antigens are recovered from the column matrix by, for example, a change in pH.

Antibodies of the invention can also be used in immunolocalization studies to analyze the presence and distribution of a polypeptide of the invention during various cellular events or physiological conditions. Antibodies can also be used to identify molecules involved in passive immunization and to identify molecules involved in the biosynthesis of non-protein antigens. Identification of such molecules can be useful in vaccine development. Antibodies of the invention, including, for example, monoclonal antibodies and single chain antibodies, can be used to monitor the course of amelioration of a disease caused by *E. canis*. By measuring the increase or decrease of *E. canis* antibodies to *E. canis* antigens in a test sample from an animal, it can be determined whether a particular therapeutic regiment aimed at ameliorating the disorder is effective. Antibodies can be detected and/or quantified using for example, direct binding assays such as RIA, ELISA, or western blot assays.

Detection

Methods of the invention can be accomplished using, for example, immunoassay techniques well known to those of skill in the art, including, but not limited to, using microplates and lateral flow devices. In one embodiment, one or more *E. canis* DIVA antigens are immobilized on a solid support at a distinct location. Detection of antigen-antibody complexes on the solid support can be by any means known in the art. For example, U.S. Pat. No. 5,726,010, which is incorporated herein by reference in its entirety, describes an example of a lateral flow device useful in the present invention. The device of the invention can be used to detect one or more antibodies to *E. canis* antigens.

Immobilization of one or more analyte capture reagents, e.g., *E. canis* polypeptides, onto a device or solid support is performed so that an analyte capture reagent will not be washed away by the sample, diluent and/or wash procedures. One or more analyte capture reagents can be attached to a surface by physical adsorption (i.e., without the use of chemical linkers) or by chemical binding (i.e., with the use of chemical linkers). Chemical binding can generate stronger attachment of capture reagents on a surface and provide defined orientation and conformation of the surface-bound molecules.

Another embodiment of the invention provides a device that is suitable for a lateral flow assay. For example, a test sample is added to a flow matrix at a first region (a sample application zone). The test sample is carried in a fluid flow path by capillary action to a second region of the flow matrix where a label capable of binding and forming a first complex with an analyte in the test sample. The first complex is carried to a third region of the flow matrix where an *E. canis* polypeptide is immobilized at a distinct location. A second complex is formed between an immobilized polypeptide and the first complex including the antibody from the sample. For example, a first complex comprising a gold sol particle and an *E. canis* polypeptide bound to an *E. canis* antibody will specifically bind and form a second complex with a second immobilized *E. canis* polypeptide or with a second antibody directed to *E. canis* antibodies. The label that is part of the second complex can be directly visualized.

In another aspect, the invention includes one or more labeled specific binding reagents that can be mixed with a test sample prior to application to a device of the invention. In this case it is not necessary to have labeled specific binding reagents deposited and dried on a specific binding reagent pad in the device. A labeled specific binding reagent, whether added to a test sample or pre-deposited on the device, can be for example, a labeled antibody that specifically binds an antibody for *E. canis*.

Any or all of the above embodiments can be provided as a kit. In one particular example, such a kit would include a device complete with specific binding reagents (e.g., a non-immobilized labeled specific binding reagent and an immobilized analyte capture reagent) and wash reagent, as well as detector reagent and positive and negative control reagents, if desired or appropriate. In addition, other additives can be included, such as stabilizers, buffers, and the like. The relative amounts of the various reagents can be varied, to provide for concentrations in solution of the reagents that substantially optimize the sensitivity of the assay. Particularly, the reagents can be provided as dry powders, usually lyophilized, which on dissolution will provide for a reagent solution having the appropriate concentrations for combining with a sample.

An *E. canis* DIVA antigen, e.g., a polypeptide, can be an immobilized analyte capture reagent in a reaction zone (solid phase). A second analyte capture reagent, e.g. an anti-IgG or anti-IgM antibody, that has been conjugated to a label, can either be added to the sample before the sample is added to the device, or the second analyte capture reagent can be incorporated into the device. For example the labeled specific binding reagent can be deposited and dried on a fluid flow path that provides fluid communication between the sample application zone and the solid phase. Contact of the labeled specific binding reagent with the fluid sample results in dissolution of the labeled specific binging reagent.

The device can also include a liquid reagent that transports unbound material (e.g., unreacted fluid sample and unbound specific binding reagents) away from the reaction zone (solid phase). A liquid reagent can be a wash reagent and serve only to remove unbound material from the reaction zone, or it can include a detector reagent and serve to both remove unbound material and facilitate analyte detection. For example, in the case of a specific binding reagent conjugated to an enzyme, the detector reagent includes a substrate that produces a detectable signal upon reaction with the enzyme-antibody conjugate at the reactive zone. In the case of a labeled specific binding reagent conjugated to a radioactive, fluorescent, or light-absorbing molecule, the detector reagent acts merely as a wash solution facilitating detection of complex formation at the reactive zone by washing away unbound labeled reagent.

Two or more liquid reagents can be present in a device, for example, a device can comprise a liquid reagent that acts as a wash reagent and a liquid reagent that acts as a detector reagent and facilitates analyte detection.

A liquid reagent can further include a limited quantity of an "inhibitor", i.e., a substance that blocks the development of the detectable end product. A limited quantity is an amount of inhibitor sufficient to block end product development until most or all excess, unbound material is transported away from the second region, at which time detectable end product is produced.

Methods of Treatment, Amelioration, or Prevention of a Disease Caused by *E. canis*

In one embodiment of the invention, a DIVA polypeptide, polynucleotide or antibody of the invention can be used to treat, ameliorate, or prevent a disease caused by *E. canis*. If, however, a DIVA polypeptide is used to treat, ameliorate, or prevent a disease caused by *E. canis*, it could not, thereafter, be used as a DIVA polypeptide for the detection and differentiation of infected, non-vaccinated, and vaccinated animals because a vaccinated animal's immune system would recognize the DIVA antigen used for vaccination. However, a DIVA polypeptide that does not cross-react with antibodies to the DIVA polypeptide used for treatment, amelioration or prevention of a disease caused by *E. canis* may still be used as an *E. canis* DIVA antigen.

For example, if SEQ ID NO:2 or a fragment thereof is used as a vaccine, then SEQ ID NOs:4, 6, 8, 10, 12, 14, 15, 16, 17 or combinations thereof can be used as a DIVA polypeptide, if they do not cross-react with antibodies specific for SEQ ID NO:2. Therefore, the DIVA polypeptides, polynucleotides, and antibodies can be used in two different ways: (1) as compositions for the prevention, treatment, or amelioration of a disease or infection caused by *E. canis*; and (2) as an *E. canis* DIVA antigen for the detection and differentiation of animals that are vaccinated; non-vaccinated; infected or not infected with *E. canis*.

Polypeptides, polynucleotides, and antibodies of the invention can be used to treat, ameliorate, or prevent a disease caused by *E. canis*. For example, an antibody, such as a monoclonal antibody of the invention or fragments thereof, can be administered to an animal, such as a human. In one embodiment of the invention an antibody or fragment thereof is administered to an animal in a pharmaceutical composition comprising a pharmaceutically acceptable carrier. A pharmaceutical composition comprises a therapeutically effective amount of an antibody or fragments thereof. A therapeutically effective amount is an amount effective in alleviating the symptoms of *E. canis* infection or in reducing the amount of *E. canis* organisms in a subject.

Polypeptides or polynucleotides of the invention can be present in an immunogenic composition and used to elicit an immune response in a host. An immunogenic composition is capable of inducing an immune response in an animal. An immunogenic polypeptide or polynucleotide composition of the invention is particularly useful in sensitizing an immune system of an animal such that, as one result, an immune response is produced that ameliorates or prevents the effect of *E. canis* infection. The elicitation of an immune response in animal model can be useful to determine, for example, optimal doses or administration routes. Elicitation of an immune response can also be used to treat, prevent, or ameliorate a disease or infection caused by *E. canis*. An immune response includes humoral immune responses or cell mediated immune responses, or a combination thereof. An immune response can also comprise the promotion of a generalized host response, e.g., by promoting the production of defensins.

The generation of an antibody titer by an animal against *E. canis* can be important in protection from infection and clearance of infection. Detection and/or quantification of antibody titers after delivery of a polypeptide or polynucleotide can be used to identify epitopes that are particularly effective at eliciting antibody titers. Epitopes responsible for a strong antibody response to *E. canis* can be identified by eliciting antibodies directed against *E. canis* polypeptides of different lengths. Antibodies elicited by a particular polypeptide epitope can then be tested using, for example, an ELISA assay to determine which polypeptides contain epitopes that are most effective at generating a strong response. Polypeptides or fusion proteins that contain these epitopes or polynucleotides encoding the epitopes can then be constructed and used to elicit a strong antibody response.

A polypeptide, polynucleotide, or antibody of the invention can be administered to a mammal, such as a mouse, rabbit, guinea pig, macaque, baboon, chimpanzee, human, cow, sheep, pig, horse, dog, cat, or to animals such as chickens or ducks, to elicit antibodies in vivo. Injection of a polynucleotide has the practical advantages of simplicity of construction and modification. Further, injection of a polynucleotide results in the synthesis of a polypeptide in the host. Thus, the polypeptide is presented to the host immune system with native post-translational modifications, structure, and conformation. A polynucleotide can be delivered to a subject as "naked DNA."

Administration of a polynucleotide, polypeptide, or antibody can be by any means known in the art, including intramuscular, intravenous, intrapulmonary, intramuscular, intradermal, intraperitoneal, or subcutaneous injection, aerosol, intranasal, infusion pump, suppository, mucosal, topical, and oral, including injection using a biological ballistic gun ("gene gun"). A polynucleotide, polypeptide, or antibody can be accompanied by a protein carrier for oral administration. A combination of administration methods can also be used to elicit an immune response. Antibodies can be administered at a daily dose of about 0.5 mg to about 200 mg. In one embodiment of the invention antibodies are administered at a daily dose of about 20 to about 100 mg.

Pharmaceutically acceptable carriers and diluents for therapeutic use are well known in the art and are described in, for example, Remington's Pharmaceutical Sciences, Mack Publishing Co. (A. R. Gennaro ed. (1985)). The carrier should not itself induce the production of antibodies harmful to the host. Such carriers include, but are not limited to, large, slowly metabolized, macromolecules, such as proteins, polysaccharides such as latex functionalized SEPHAROSE®, agarose, cellulose, cellulose beads and the like, polylactic acids, polyglycolic acids, polymeric amino acids such as polyglutamic acid, polylysine, and the like, amino acid copolymers, peptoids, lipitoids, and inactive, avirulent virus particles or bacterial cells. Liposomes, hydrogels, cyclodextrins, biodegradable nanocapsules, and bioadhesives can also be used as a carrier for a composition of the invention.

Pharmaceutically acceptable salts can also be used in compositions of the invention, for example, mineral salts such as hydrochlorides, hydrobromides, phosphates, or sulfates, as well as salts of organic acids such as acetates, proprionates, malonates, or benzoates. Especially useful protein substrates are serum albumins, keyhole limpet hemocyanin, immunoglobulin molecules, thyroglobulin, ovalbumin, tetanus toxoid, and other proteins well known to those of skill in the art. Compositions of the invention can also contain liquids or excipients, such as water, saline, phosphate buffered saline, Ringer's solution, Hank's solution, glucose, glycerol, dextrose, malodextrin, ethanol, or the like, singly or in combination, as well as substances such as wetting agents, emulsifying agents, tonicity adjusting agents, detergent, or pH buffering agents. Additional active agents, such as bacteriocidal agents can also be used.

If desired, co-stimulatory molecules, which improve immunogen presentation to lymphocytes, such as B7-1 or B7-2, or cytokines such as MIP1α, GM-CSF, IL-2, and IL-12, can be included in a composition of the invention. Optionally, adjuvants can also be included in a composition. Adjuvants are substances that can be used to nonspecifically augment a specific immune response. Generally, an adjuvant and a polypeptide of the invention are mixed prior to presentation to the immune system, or presented separately, but are presented into the same site of the animal. Adjuvants can include, for example, oil adjuvants (e.g. Freund's complete and incomplete adjuvants) mineral salts (e.g. $Alk(SO_4)_2$; $AlNa(SO_4)_2$, $AlNH_4(SO_4)$, Silica, Alum, $Al(OH)_3$, and $Ca_3(PO_4)_2$), polynucleotides (i.e. Polyic and Poly AU acids), and certain natural substances (e.g. wax D from *Mycobacterium tuberculosis*, as well as substances found in *Corynebacterium parvum*, *Bordetella pertussis* and members of the genus *Brucella*. Adjuvants which can be used include, but are not limited to MF59-0, aluminum hydroxide, N-acetyl-muramyl-L-threonyl-D-isoglutamine (thr-MDP), N-acetyl-nor-muramyl-L-alanyl-D-isoglutamine (CGP 11637), referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/TWEEN® (polysorbate) 80 emulsion.

The compositions of the invention can be formulated into ingestible tablets, buccal tablets, troches, capsules, elixirs, suspensions, syrups, wafers, injectable formulations, mouthwashes, dentrifices, and the like. The percentage of one or more polypeptides, polynucleotides, or antibodies of the invention in such compositions and preparations can vary from 0.1% to 60% of the weight of the unit.

Administration of polypeptides, polynucleotides, or antibodies can elicit an immune response in the animal that lasts for at least 1 week, 1 month, 3 months, 6 months, 1 year, or longer. Optionally, an immune response can be maintained in an animal by providing one or more booster injections of the polypeptide, polynucleotide, or antibodies at 1 month, 3 months, 6 months, 1 year, or more after the primary injection. If desired, co-stimulatory molecules or adjuvants can also be provided before, after, or together with the compositions.

A composition of the invention comprising a polypeptide, polynucleotide, antibody, or a combination thereof is administered in a manner compatible with the particular composition used and in an amount that is effective to elicit an immune response as detected by, for example, an ELISA. A polynucleotide can be injected intramuscularly to a mammal, such as a baboon, chimpanzee, dog, or human, at a dose of 1 ng/kg, 10 ng/kg, 100 ng/kg, 1000 ng/kg, 0.001 mg/kg, 0.1 mg/kg, or 0.5 mg/kg. A polypeptide or antibody can be injected intramuscularly to a mammal at a dose of 0.01, 0.05, 0.5, 0.75, 1.0, 1.5, 2.0, 2.5, 5 or 10 mg/kg.

Polypeptides, polynucleotides, or antibodies, or a combination thereof can be administered either to an animal that is not infected with *E. canis* or can be administered to an *E. canis*-infected animal. The particular dosages of polynucleotide, polypeptides, or antibodies in a composition will depend on many factors including, but not limited to the species, age, gender, concurrent medication, general condition of the mammal to which the composition is administered, and the mode of administration of the composition. An effective amount of the composition of the invention can be readily determined using only routine experimentation.

All patents, patent applications, and other scientific or technical writings referred to anywhere herein are incorporated by reference in their entirety. The invention illustratively described herein suitably can be practiced in the absence of any element or elements, limitation or limitations that are not specifically disclosed herein. Thus, for example, in each instance herein any of the terms "comprising", "consisting essentially of", and "consisting of" can be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

EXAMPLES

Example 1

Preparation of Formalin Killed *E. Canis* for Immunization into Dogs

*E. canis* was grown in canine cell culture using methods described in the literature. See e.g., Breitschwerdt, Antimicrobial Agents and Chemotherapy, 1998, Vol 42:362-368. Using light microscopy, 030 cells were estimated to be greater than 80% infected by *E. canis*. Two liters of *E. canis* infected cell culture were collected, centrifuged and the pellet retained yielding 7.31 gms of material (wet weight). It is presumed water made up 80% of the weight of the material, giving an estimated dry weight of 1.462 gms (20% of the weight of the material). The cell pellet was resuspended to 20 mg/ml in PBS (dry weight) for a total volume of 73 ml.

To this resuspended cell pellet, 0.73 ml of formalin solution was added (Sigma Catalog HT50-1-2 Formalin Solution 10%, neutral buffered) for a final formaldehyde concentration of 0.04%. The solution was stirred overnight at 4° C. The inactivated mixture was centrifuged and the cell pellet retained. The pellet was washed by resuspension into 250 mls of PBS. The material was collected by centrifugation and the wash was repeated one time.

The washed cell pellet was resuspended into 73 mls of PBS. The sample was aliquoted to 73 screw cap vials and frozen at −80° C. Each vial contains 20 mgs (dry weight) of formalin inactivated *E. canis* cell culture, suitable for combining with the appropriate adjuvant for immunization into animals.

Example 2

Preparation of Formalin Fixed *E. canis* with Two Different Adjuvants, Protocol for the Immunization of Beagles with *E. canis* Antigen, and Testing of Sera from Immunized Beagles Using SNAP® 3Dx® Reversible Flow Chromatographic Assay The preparation of antigen with aluminum hydroxide adjuvant is a technique well known to those skilled in the art. For example see "Antibodies, A Laboratory Manual", Cold Spring Harbor Press, 1988, pp 99.

For immunization into dogs (laboratory beagles), two sets of doses were prepared with aluminum hydroxide adjuvant prepared as described above and two sets of doses were prepared with Ribi adjuvant (Corixa Corp., Seattle Wash.) using the protocol described by the manufacturer. Each dose contained approximately 20 mg of formalin inactivated *E. canis* cell culture (dry weight).

Kennel kept laboratory beagles were selected for immunization with the *E. canis* formalin inactivated antigen. Two groups of two dogs each; with each group using a different adjuvant were dosed with the formalin fixed *E. canis* preparation (aluminum oxide or Ribi). On day 0 all 4 dogs were found to be sero-negative using both the SNAP® 3Dx® reversible flow chromatographic assay diagnostic as well as Western blot analysis using *E. canis* organism.

The IACUC committee of Covance Research Products Inc. approved the protocol for immunization of laboratory beagles. Dogs were challenged on days 0, 28 and 56 with weekly 1 ml bleeds being monitored using SNAP® 3Dx® reversible flow chromatographic assay. All dogs were dosed with the appropriate test article subcutaneously in the dorsoscapular area. All four animals seroconverted to a positive test on SNAP®3Dx® reversible flow chromatographic assay (*E. canis*) by day 42. Production bleeds were taken on days 42 and 70 (approximately 50 ml blood that yielded approximately 25 ml sera).

FIG. 1 shows SNAP®3Dx® reversible flow chromatographic assay evaluation of laboratory beagles. The SNAP® reversible flow chromatographic assay device was used as described by manufacturer. "Pre" sample is from day 0. "Post" sample is from day 42. The *E. canis* positive spot becomes positive in all 4 dogs for the day 42 sample. Similar results were observed for the day 70 sample.

Experiments with a third vaccine comprising a third adjuvant, BCG, (Calbiochem of EMD Biosciences, Inc. San Diego, Calif.) revealed similar results. Preparation of the third vaccine was identical to the preparations described for the Ribi adjuvante vaccine described above except: 1) formalin inactivation was for 24 hrs at 4 C, and 2) 1 mg of BCG was added. The vaccination schedule was day 0, day 14, with weekly bleeds assayed for reactivity with *E. canis* proteins.

Example 3

Enrichment of *E. Canis* from Cell Culture Using PERCOLL® (Colloidal Silica Coated With Polyvinylpyrrolidone) Gradients For DNA isolation and Western blot analysis, *E. canis* was enriched from cell culture using PERCOLL® (colloidal silica coated with polyvinylpyrrolidone) density gradients. The process of isolating intracellular pathogens from cell culture, such as *Ehrlichia*, is a technique well known to those skilled in the art. For example, see Akira et al. (1982) Purification of *Rickettsia tsutsugamushi* by PERCOLL® density gradient centrifugation, Microbiol. Immunol., 26:321-328.

A typical *E. canis* enrichment began with 1.5 liters of infected cell culture (see above). The cells were centrifuged 6,000×g, the cell pellet retained and the supernatant discarded. The cell pellet was resuspended into 20 ml of PBS that was followed by a second centrifugation. The supernatant was discarded and supernatant retained. The pellet was then resuspended into 20 ml of PBS, sonicated for 5 seconds at 20 kHz, power setting 1.5 using a Branson sonicator. The sample was then centrifuged at 500×g for 5 minutes to pellet large debris.

PERCOLL® (colloidal silica coated with polyvinylpyrrolidone) was added to the supernatant to a final concentration of 32% (4.5 ml of PERCOLL® (colloidal silica coated with polyvinylpyrrolidone) with 10 ml of sample). The sample was loaded into Oak Ridge tubes compatible with a 70.1 Ti ultracentrifuge rotor, and centrifuged for 30 minutes at 63,000×g. The opaque band was collected using a Pasteur pipette. The opaque band is highly enriched for *Ehrlichia* (confirmed using light microscopy of the collected sample). After a 1:4 dilution with PBS, the sample was aliquoted and centrifuged at 12,000×g. The supernatant was discarded and the *Ehrlichia* pellet stored at −80° C.

Example 4

Testing of Sera or Plasma from Challenged and Infected Dogs by Western Blot

The use of 1-dimensional SDS-PAGE gel analysis and 2-dimensional gel analysis ($1^{st}$ dimension isoelectric focusing, $2^{nd}$ dimension SDS-PAGE) is well known to those skilled in the art. For example see Current Protocols in Molecular Biology, eds. F. M. Ausubel et al., John Wiley & Sons Inc., 1997, pages 10.2.2-10.3.11. The use of Western blots to analyze proteins separated using these methods are well known to those skilled in the art. For example see Current Protocols in Molecular Biology, eds. F. M. Ausubel et. al., John Wiley & Sons Inc., 1997, pages 10.8.1-10.8.116.

Figure 2:
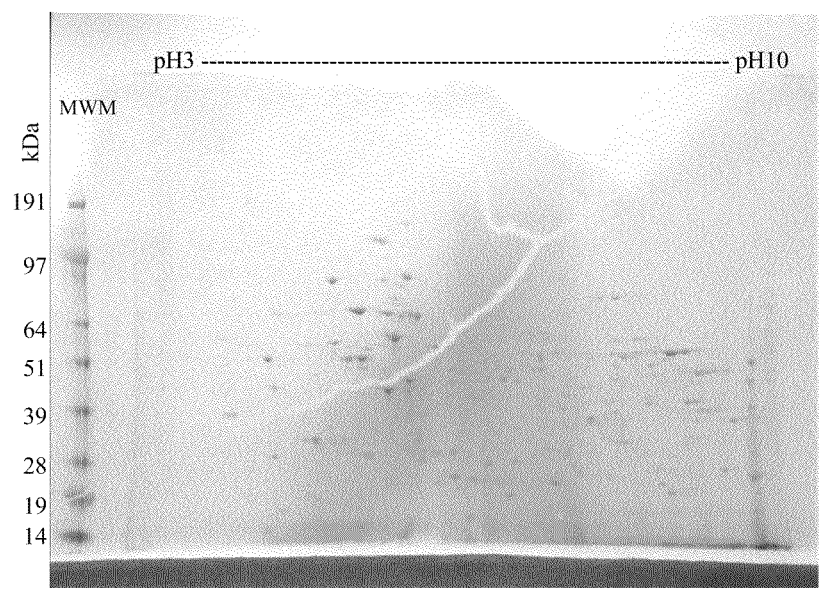
FIG. 2 shows a gel of *E. canis* proteins separated using 2D gel electrophoresis. Stained with BIOSAFE™ Coomassie Blue (Bio-Rad Inc.).
Figure 3:
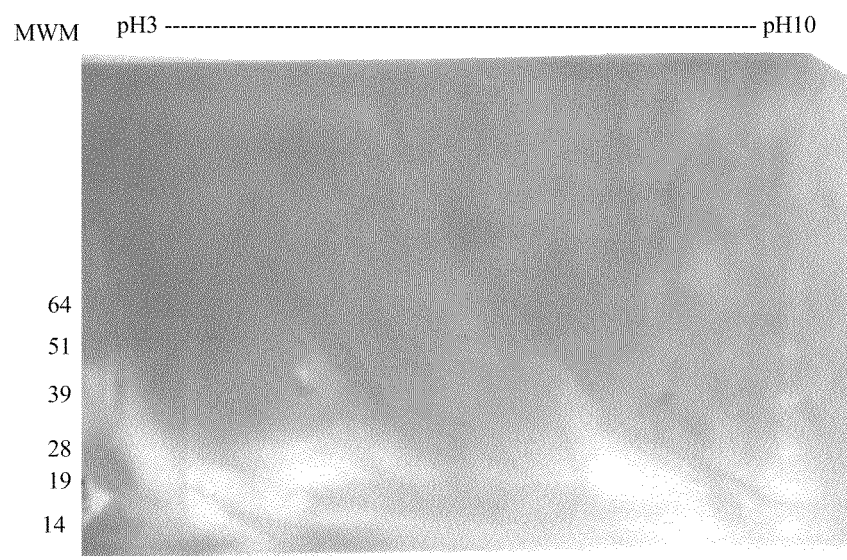
FIG. 3 shows a Western blot of *E. canis* proteins using dog sera harvested at day 0. The plasma dilution is 1:100. These dogs were negative for reactivity with *E. canis* antigens.
Figure 4:
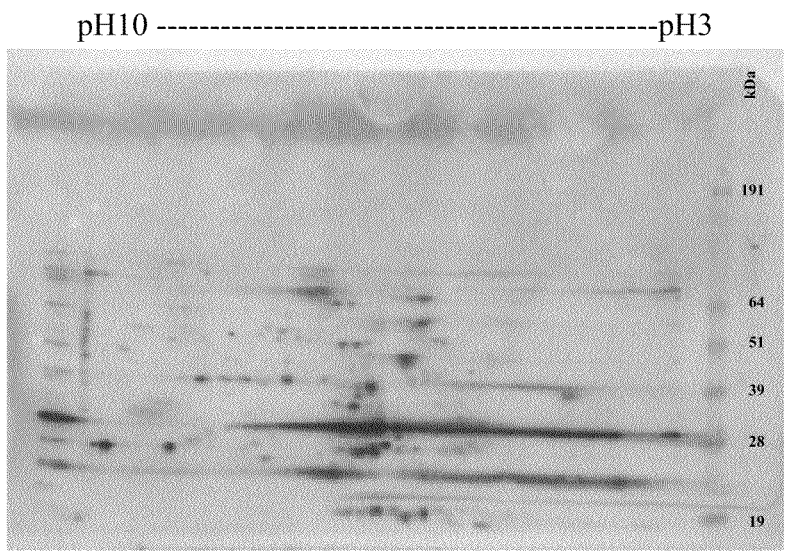
FIG. 4 shows a Western blot of *E. canis* proteins using dog sera from a pool of four challenged animals. The sera dilution is 1:100.
Figure 5:
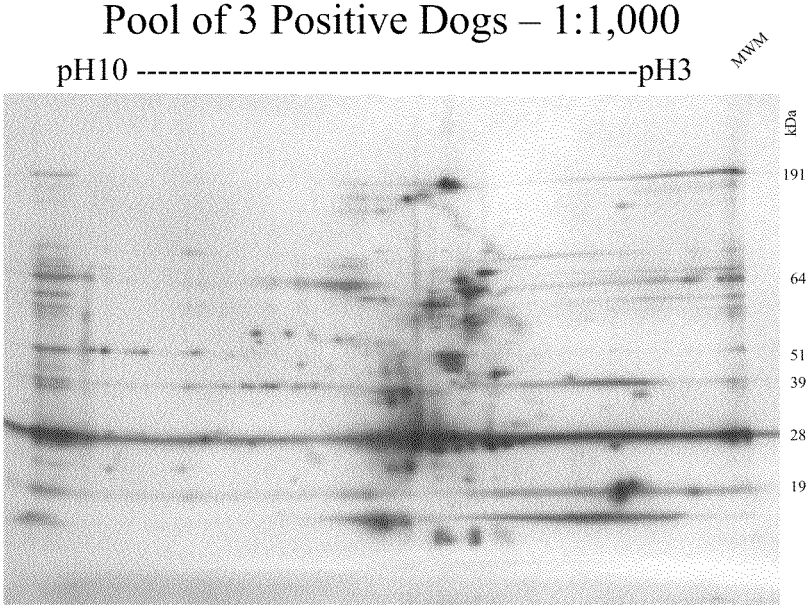
FIG. 5 shows a Western blot of *E. canis* proteins using dog plasma from a pool of infected animals. The sera dilution is 1:1000.

Initial work was performed using Western analysis of proteins separated with 1D gels (data not shown), followed by Western analysis of proteins separated using 2D gels. Proteins from whole *E. canis* harvested from cell culture were analyzed using 2D gel electrophoresis (materials and reagents used as described by the manufacturer; Bio-Rad Life Sciences Research, Hercules, Calif. 94547). The amount of sample to load per gel was determined empirically (see FIG. 2). The proteins were blotted to nitrocellulose and probed using canine sera from laboratory beagles at day 0, dogs challenged with formalin fixed *E. canis* antigen (see above), or sera from animals infected with *E. canis* (see FIGS. 3, 4 & 5).

Positive canine sera and plasma was isolated from dogs infected with *E. canis*. *E. canis* infection was verified by Western analysis of lymphocytes harvested from whole blood from these dogs, and confirmed by use of the IDEXX SNAP®3Dx® reversible flow chromatographic assay with canine sera or plasma (commercially available from IDEXX Laboratories Inc., used as described by the manufacturer).

For Western blot analysis proteins were separated using 1D SDS-PAGE or 2D isoelectric focusing/SDS-PAGE gels followed by electo-blotting of the proteins from the gels to nitrocellulose. The nitrocellulose blots were incubated in a blocking solution of 2.5% non fat dry milk dissolved into Tris buffered saline (pH 7.5), 0.05% TWEEN® (polysorbate) 20. Canine sera or plasma was diluted to the titer as described into buffer containing an *E. coli* lysate to block non-specific binding with 30% normal calf sera and incubated for 2 hrs at room temperature or over night at 4° C. After washing 3 times in TBS-TWEEN® (polysorbate) (0.05%), the blots were transferred to a buffer containing 50% fetal calf sera, 50% TBS-TWEEN® (polysorbate)-Kathon (0.05% & 0.5% respectively) to prevent nonspecific binding of a rabbit anti-canine Fc polyclonal antibody conjugated to horseradish peroxidase (Jackson Immuno Research, West Grove, Pa. 19390). The rabbit anti-canine Fc polyclonal antibody conjugate was diluted 1:5,000. The gels were washed 3 times with TBS TWEEN® (polysorbate) (0.05%), one time with TBS, and the presence of HRP detected using ECL Western Blotting Detection Reagents (Amersham Biosciences, Piscataway, N.J. 08855-1327) used as described by manufacturer. Digital images of exposed X-ray film were captured using a GelDoc 2000 (Bio-Rad Inc.).

Example 5

Isolation of DNA from *E. canis* and Construction of a Lambda Expression Library and Screening of the *E. canis* Lambda Expression Library for Clones Having DIVA Activity The preparation and screening of lambda expression libraries is a technique well known to those skilled in the art. For example, see Current Protocols in Molecular Biology, eds. F. M. Ausubel et al., John Wiley & Sons Inc., 1997, pages 5.1 through 5.8.6. For the construction of the expression library, genomic DNA was purified from *E. canis* isolated from cell culture by PERCOLL® (colloidal silica coated with polyvinylpyrrolidone) gradient centrifugation (see above). DNA was purified using a genomic DNA purification kit from Qiagen Sciences (Germantown, Md.). A Lambda ZAP® II predigested EcoRI/CIAP Vector Kit (Stratagene Corp., La Jolla, Calif. 92037) was used as specified by the manufacturer for construction of the library. *E. canis* genomic DNA was partially digested with TSP509 and fragments ranging from 2-6 kb were isolated using agarose gel electrophoresis and ligated into the lambda vector. Phage were packaged and grown as specified by the manufacturer.

Approximately 120,000 individual lambda plaques were screened for binding to sera isolated from dogs identified as positive for infection with *E. canis*, but negative for reactivity with sera from animals challenged with an *E. canis* grown in cell culture (see above). From the initial screen 84 individual plaques were identified as having this activity.

Lambda plaques were subjected to two rounds of plaque purification and retested to verify positive reactivity with sera from *E. canis* infected animals, negative reactivity when screened with sera from challenged animals.

Isolated lambda plaques were screened for cross reactivity with sera from animals identified as being seropositive for *Anaplasma phagocytophilia*, *Borrelia burgdorferi* (causative agent of Lyme disease), *Rickettsia rickettsii* (causative agent of Rocky Mountain Spotted Fever), *Leptospira interrogans* and *Dirofilaria immitis* (causative agent of canine heartworm).

At the end of the screening process, 43 lambda plaques were found to react with sera from animals infected with *E. canis* that did not react with challenge sera or sera from dogs infected with other canine pathogens (see above).

Using the ZAP® feature of the cloning vector as per the manufacturers instructions, inserts into the lambda vector were converted to plasmids. The plasmids were transformed into the *E. coli* strain XL-1 blue for protein expression and analysis of encoded proteins by Western blot. The ends of the *E. canis* DNA inserts were subjected to DNA sequence analysis using T7 and T3 sequencing primers.

Sequence information from both the T7 and T3 reactions for all 43 clones was submitted for BLAST analysis to the NCBI website. Results were tabulated in an excel format. Based on sequence identity between the clone and the available shotgun genome sequence for *E. canis* (NCBI: NZ_AAEJ01000001), segments of genomic DNA for each clone were identified. Individual clones sharing common genes were grouped for further analysis by Western blot using pools of infected and bacterial-challenged canine sera. Based on similar banding patterns, duplicate clones were eliminated. Any clones showing reactivity to both sets of sera were eliminated. As a result of this analysis, 23 clones were selected for further evaluation. The grouping of the clones and the common antigen per group is shown in Table 1.

TABLE 1

| Common Antigen | Clone Number(s) |
| --- | --- |
| 120 kDa Antigen | 2, 10, 17, 33, 35, 79 |
| Heat Shock Proteins | 4, 9, 24, 66 |
| ATPase | 7, 84 |
| Ribosomal Protein L1 | 21, 47, 65 |
| 200 kDa Antigen | 26, 55, 76 |
| Hypothetical Protein | 75 |
| Pyruvate Dehydrogenase | 5 |
| Ribosomal Protein (50S) | 6 |
| Unknown | 57 |
| Transcriptional Regulator | 82 |

Example 6

Western Blot Analysis Using Individual *E. canis* Positive Canine Serum Samples

Figure 6:
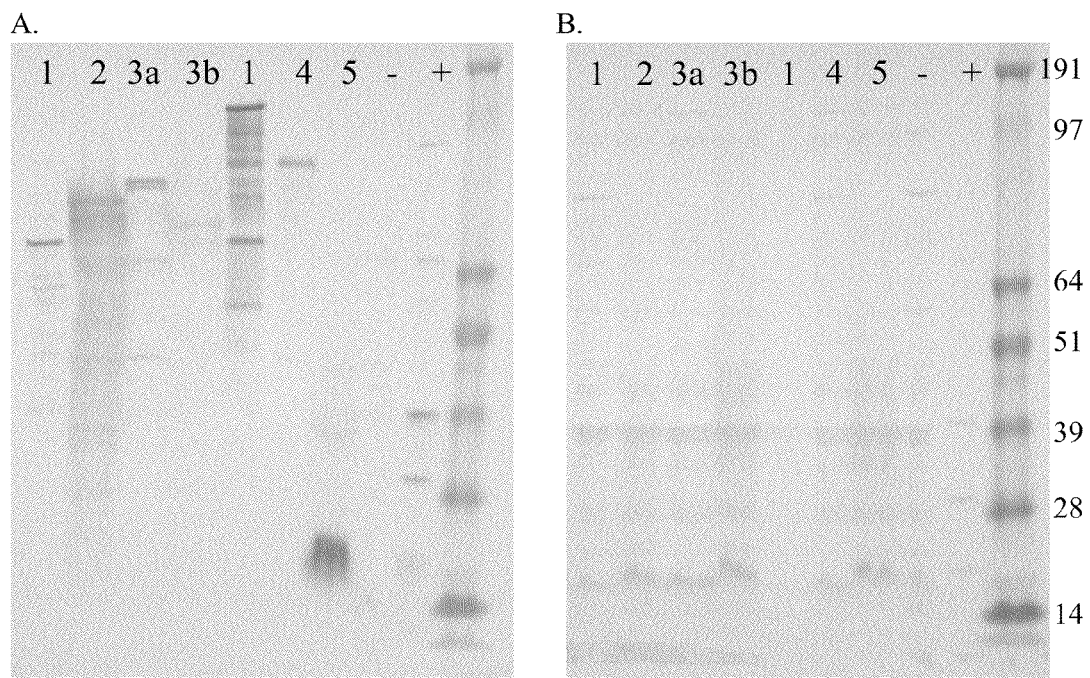
FIG. 6 shows a Western blot of six different *E. canis* DIVA antigens expressed in *E. coli* and probed with either dog sera from a pool of four infected animals (A) or dog sera pooled from four challenged animals (B). Sera dilutions were 1:100 for challenged animals or 1:500 for the infected animals. The DIVA antigens represented include: (1) 200 kDa antigen, (2) Ribosomal protein L1, (3a and 3b) "ATPase"—two different segments, (4) 120 kDa antigen, (5) Heat shock proteins/p16 antigen.

All 23 clones were analyzed on individual SDS-PAGE gels. Each gel was transferred to nitrocellulose and subjected to Western blotting using individual samples of canine sera from dogs that were only positive for *E. canis* infections by ELISA/SNAP® (reversible flow chromatographic assay) testing. Canine serum was diluted 1:500 in the same diluent described in Example 4 containing *E. coli* lysate and reactivity was detected using standard colorometric horseradish peroxidase techniques (Opti-4CN, Bio-Rad). A total of thirteen individual canine serum samples were evaluated. Blots were compared across samples to determine the number of dogs showing reactivity to a predominant band or set of bands per clone. The results are summarized in Table 2 and FIG. 6 (clones listed in bold are depicted in the figure).

TABLE 2

| Common Antigen | Clone Number(s) | Positive Reactors |
| --- | --- | --- |
| 120 kDa Antigen | 2, 10, 17, 33, 35 | 13/13 |
| Heat Shock Proteins | 9 | 12/13 |
| ATPase | 7, 84 | 12/13 |
| Ribosomal Protein L1 | 21, 47, 65 | 12/13 |
| 200 kDa Antigen | 26, 55, 76 | 12/13 |

All 23 clones were also analyzed by Western blot using pooled canine sera that had tested positive for other vector-borne infectious diseases. Samples testing positive by ELISA or SNAP® (reversible flow chromatographic assay) for the following single infections were evaluated: Heartworm, Lyme, *Anaplasma phagocytophilum*, or *E. ewingii*. None of the clones identified in the table above showed cross-reactivity with positive canine sera for these other vector-borne infections.

Example 7

Identification of Relevant Gene Segments Encoding *E. canis* DIVA Antigens a. 120 kDa Antigen This antigen were previously described by Yu et al. (J Clin Microbiol. 2000 January; 38(1):369-74) and shown to be useful in the diagnosis of *E. canis* infections in dogs. The accession number for this gene is AF112369 and the associated protein is AAD34330. Clones 2, 10, 17, and 33 contain full-length segments of the 120 kDa antigen gene. Clone 35 may contain a truncation of this gene. (See SEQ ID NOs:1 and 2).

This gene was amplified from *E. canis* genomic DNA and subcloned into a pET expression system with a 6-His tag according to the manufacturer's instructions (Invitrogen). Sequencing results of this plasmid exactly matched the gene sequence encoding the protein shown in SEQ NO:ID 2, from amino acids 58 to 589. Protein lysates from BL21 bacteria induced to express this protein were analyzed by Western blotting with infected canine sera and compared to Western blots probed with sera from animals challenged with culture-adapted organisms. Consistent with previous findings, only sera from infected dogs recognized this protein of the expected molecular weight (data not shown).

P120 has a 36 amino acid motif that is repeated 14 times. See, FIG. 8, SEQ ID NO:15. The repeated portion (underlined region in FIG. 8) is a 60 kD peptide. FIG. 9A shows the aligned 14 repeats (SEQ ID NO:16). FIG. 9B shows the consensus sequence of the 14 repeats (SEQ ID NO:17).

One embodiment of the invention provides a polypeptide comprising:

(SEQ ID NO: 17)
KEEX$_1$TPEVX$_2$AEDLQPAVDX$_3$SX$_4$EHSSSEVGX$_5$KVSX$_6$TS.

Where $X_1$=S or N $X_2$=K or R $X_3$=G, D, or S $X_4$=V or I $X_5$=E or K $X_6$=E or K Another embodiment of the invention provides a multimeric polypeptide where SEQ ID NO:17 is repeated two or more times. The multimeric polypeptide can also comprise one or more heterologous polypeptides.

b. 200 kDa Antigen

This antigen was previously described by McBride et al. (J Clin Microbiol. 2001 January; 39(1):315-22) and shown to be useful in the diagnosis of ehrlichiosis. The accession number for this gene is AF252298 and associated protein AAK01145. A portion of this protein sequence is associated with a published patent (SEQ ID NO:2 of U.S. Pat. No. 6,355,777, accession number AAE96254). We have identified a different region of this protein that serves as diagnostic antigen for ehrlichiosis and a DIVA reagent. The portion of the gene spans from nucleotide 1081 of AF252298 through to the end, nucleotide 4266. (See SEQ ID NOs:3 and 4).

This gene was amplified from *E. canis* genomic DNA and subcloned into a pET expression system with a 6-His tag according to the manufacturer's instructions (Invitrogen). Sequencing results of this plasmid exactly matched the gene sequence encoding the protein shown in SEQ ID NO:4, from amino acids 1 to 1061. Protein lysates from BL21 bacteria induced to express this protein were analyzed by Western blotting with infected canine sera and compared to Western blots probed with sera from animals challenged with culture-adapted organisms. Consistent with previous findings, only sera from infected dogs recognized this protein of the expected molecular weight (data not shown).

c. ATPase

This gene (Locus tag "Ecan02000699") has been predicted by automated computational analysis of the shotgun genome sequence of *E. canis*. It codes for a protein of more than 4000 amino acids (ZP_00210575). The *E. canis* DIVA screen identified two separate regions of this gene and its associated protein as potential immunodominant antigens and DIVA reagents. The segments of the protein identified in clones 84 and 7 are amino acids 1984-2774 and 2980-3740, respectively, of accession number 46308382. (See SEQ ID NOs: 5, 6, 7, 8).

Both fragments of this gene was amplified from *E. canis* genomic DNA and subcloned separately into a pET expression system with a 6-His tag according to the manufacturer's instructions (Invitrogen). Sequencing results of this plasmid exactly matched the gene sequences associated with the proteins shown SEQ ID NOs:6 and 8, from amino acids 1 to 782 and 1 to 746 respectively. Protein lysates from BL21 bacteria induced to express these proteins were analyzed by Western blotting with infected canine sera and compared to Western blots probed with sera from animals challenged with culture-adapted organisms. Consistent with previous findings, only sera from infected dogs recognized these proteins of the expected molecular weight (data not shown).

d. Heat Shock Proteins

Although this clone contained a gene for the heat shock protein, GrpE, the gene sequence coding for the immunodominant antigen arises from a hypothetical protein sequence predicted by the automated computational analysis of the genome. Based on the molecular weight and pI of the protein, the gene of interest in clone 9 is locus number "Ecan02000495" and the associated protein 46308954.

Because this protein is only predicted from the computer annotation of the genome and has not been previously identified from *E. canis* organisms as an immunodominant protein, this is the first evidence that this gene is expressed in *E.*

*canis* and stimulates an immune response in the infected canine host. The protein will be identified as the p16 antigen (see SEQ ID NO: 9 and 10).

Figure 7:
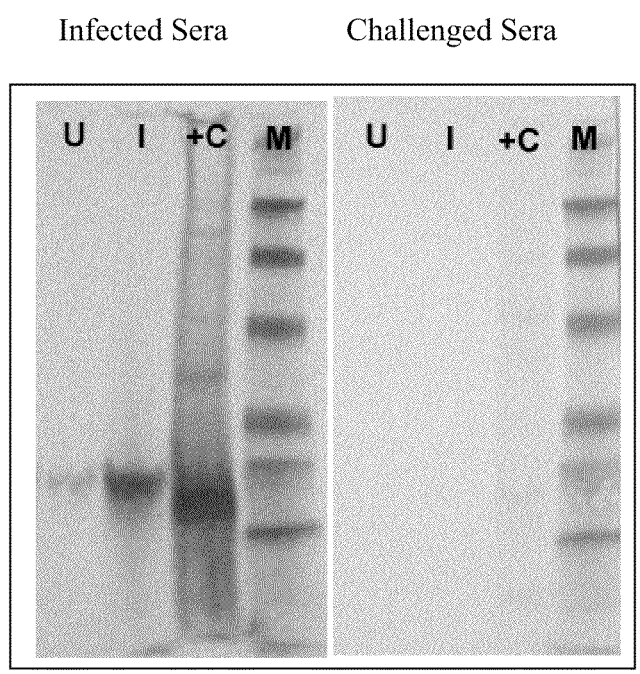
FIG. 7 demonstrates that cloned p16 antigen is recognized by sera from dogs infected with *E. canis* but not those challenged with the cultured organism. Lysates from uninduced (U) or induced (I) bacteria transformed with a vector expressing the p16 antigen or the original genomic fragment (+C) were separated by SDS-PAGE and transferred to nitrocellulose for Western blot analysis.

This gene was amplified from the pBlueScript vector containing the genomic DNA of interest and subcloned into a pET expression system with a 6-His tag according to the manufacturer's instructions (Invitrogen). Sequencing results of this plasmid exactly matched the gene sequence associated with locus number "Ecan02000495". Protein lysates from BL21 bacteria induced to express this protein were analyzed by Western blotting with infected canine sera and compared to Western blots probed with sera from animals challenged with culture-adapted organisms. Consistent with previous findings, only sera from infected dogs recognized this protein of the expected molecular weight (see FIG. 7).

e. Ribosomal Protein L1

This gene is identified by the locus tag "Ecan02000476" from the *E. canis* genome. The associated protein has the accession number ZP_00211130 (see SEQ ID NOs:11 and 12). The identification of this protein has been predicted based on automated computational analysis of the genome. A BLAST analysis of this protein reveals that the sequence is about 70% identical to a surface protein of *E. chaffeensis* (Accession number 4894576). Immunoreactivity to the *E. chaffeensis* protein has previously been reported by Yu et al., (J Clin Microbiol. 1999 August; 37(8):2568-75). The *E. chaffeensis* protein (Accession number 4894576) is referred to as the 106 kDa protein precursor.

f. Possible Non-120 kDa Antigens

Within the genomic fragment containing the gene for the 120 kDa antigen, other genes are present that may also be immunodominant and DIVA reagents. For instance, clone 10 produces a different banding pattern on Western blots probed with infected sera, compared to clones containing the 120 kDa antigen alone. Clone 10 contains genetic information for the VirD4 components of a Type IV secretory pathway and this gene sequence is identified by the locus tag "Ecan02000624". This gene codes for a protein of 723 amino acids (ZP_00211244), but only a portion of this protein appears to be expressed by clone 10, as determined by the molecular weight of the protein identified on the gel (see SEQ ID NOs:13 and 14).

We claim:

1. A method of distinguishing between animals that have been vaccinated with inactivated *Ehrlichia canis* cells that (1) have been infected with *Ehrlichia canis* and animals that have been vaccinated with inactivated *E. canis* cells that (2) have not been infected with *E. canis*, the method comprising:
   (a) contacting individual biological samples from one or more animals vaccinated for *E. canis* with one or more purified wild-type *E. canis* polypeptides that do not specifically bind to antibodies that are a component of the animals' immune response to an inactivated *E. canis* cell vaccine, wherein the one or more purified wild-type *E. canis* polypeptides specifically bind to antibodies that are a component of the animals' immune response to an *E. canis* infection; and (b) detecting whether antibodies in the one or more samples specifically bind to the one or more purified wild-type *E. canis* polypeptides; wherein if antibodies in the one or more samples specifically bind to the one or more purified wild-type *E. canis* polypeptides, then those animals have been infected with *E. canis*; and (c) differentiating animals that have been infected with *E. canis* from animals that have not been infected with *E. canis*, based on the results of step (b);

whereby animals that have been vaccinated with inactivated *E. canis* cells that (1) have been infected with *Ehrlichia canis* and animals that have been vaccinated with inactivated *E. canis* cells that (2) have not been infected with *E. canis* are distinguished.

2. The method of claim 1, wherein the one or more wild-type purified *E. canis* polypeptides are linked to an amino acid sequence to which the one or more purified *E. canis* polypeptides are not associated with in nature.

3. The method of claim 1, wherein the one or more wild-type purified *E. canis* polypeptides are linked to an indicator reagent, an amino acid spacer, an amino acid linker, a signal sequence, a stop transfer sequence, a transmembrane domain, a protein purification ligand, or a combination thereof.

4. The method of claim 1, wherein the one or more wild-type purified *E. canis* polypeptides are present in a fusion protein.

5. The method of claim 1, wherein the one or more wild-type purified *E. canis* polypeptides are in multimeric form.

6. The method of claim 1, wherein the one or more wild-type purified *E. canis* polypeptides are immobilized to a solid support.

7. A method of distinguishing between animals that (1) have been infected with *Ehrlichia canis* and animals that (2) have not been infected with *E. canis* regardless of whether the animals have been vaccinated for *E. canis* with inactivated *E. canis* cells, the method comprising:

(a) contacting a biological sample from an animal with one or more purified *E. canis* polypeptides wherein the one or more purified *E. canis* polypeptides consist of SEQ ID NO:2, 16, 17, or combinations thereof, wherein the one or more purified *E. canis* polypeptides are optionally:

(i) linked to an amino acid sequence to which the one or more purified *E. canis* polypeptides are not associated with in nature; or (ii) linked to an indicator reagent, an amino acid spacer, an amino acid linker, a signal sequence, a stop transfer sequence, a transmembrane domain, a protein purification ligand, or a combination thereof; and (b) detecting whether antibodies in the sample specifically bind to the one or more purified *E. canis* polypeptides; wherein if antibodies in the sample specifically bind to the one or more purified *E. canis* polypeptides, then the animal has been infected with *E. canis;* whereby animals that (1) have been infected with *Ehrlichia canis* and animals that (2) have not been infected with *E. canis* regardless of whether the animals have been vaccinated for *E. canis* with inactivated *E. canis* cells are distinguished.

8. The method of claim 7, wherein the one or more purified *E. canis* polypeptides are immobilized to a solid support.

9. A method of distinguishing between an animal that has been infected with *E. canis* from an animal that has not been infected with *E. canis*, the method comprising:

(a) contacting a biological sample from an animal with one or more purified polypeptides consisting of SEQ ID NO:2, 15, 16, 17, or combinations thereof, wherein, optionally, (i) the one or more purified *E. canis* polypeptides are linked to an indicator reagent, an amino acid spacer, an amino acid linker, a signal sequence, a stop transfer sequence, a transmembrane domain, a protein purification ligand, or a combination thereof; (ii) the one or more purified *E. canis* polypeptides are linked to an amino acid sequence to which the one or more purified *E. canis* polypeptides are not associated with in nature; (iii) the one or more purified *E. canis* polypeptides are present in a fusion protein; or (iv) one or more purified *E. canis* polypeptides are in multimeric form; and (b) detecting whether antibodies in the sample specifically bind to the one or more purified polypeptides;

wherein if antibodies in the sample specifically bind to the one or more purified polypeptides, then the animal has been infected with *E. canis.*

10. The method of claim 9, wherein the one or more purified *E. canis* polypeptides are immobilized to a solid support.

11. A method of determining whether an animal has been infected with *Ehrlichia canis*, the method comprising:

(a) obtaining a biological sample from an animal that has been vaccinated with inactivated *E. canis* cells;

(b) contacting the biological sample with one or more wild-type purified *E. canis* polypeptides that do not specifically bind to antibodies that are a component of the animal's immune response to an inactivated *E. canis* cell vaccine, wherein the one or more wild-type purified *E.* canis polypeptides specifically bind to antibodies that are a component of the animal's immune response to an *E. canis* infection; and (c) detecting whether antibodies in the sample specifically bind to the one or more wild-type purified *E. canis* polypeptides, and (d) recognizing that the *E. canis* infection status result of the method is not affected by a vaccination of the animal with inactivated *E. canis* cells, whereby if antibodies in the sample specifically bind to the one or more wild-type purified *E. canis* polypeptides, then the animal has been infected with *Ehrlichia canis*.

12. The method of claim 11, wherein the one or more wild-type purified *E. canis* polypeptides are linked to an amino acid sequence to which the one or more purified *E. canis* polypeptides are not associated with in nature.

13. The method of claim 11, wherein the one or more wild-type purified *E. canis* polypeptides are linked to an indicator reagent, an amino acid spacer, an amino acid linker, a signal sequence, a stop transfer sequence, a transmembrane domain, a protein purification ligand, or a combination thereof.

14. The method of claim 11, wherein the one or more wild-type purified *E. canis* polypeptides are present in a fusion protein.

15. The method of claim 11, wherein the one or more wild-type purified *E. canis* polypeptides are in multimeric form.

16. The method of claim 11, wherein the one or more wild-type purified *E. canis* polypeptides are immobilized to a solid support.

17. The method of claim 11, wherein the one or more wild-type purified *E. canis* polypeptides consist of SEQ ID NO:2, 15, 16, 17, or combinations thereof.

18. The method of claim 1, wherein one or more wild-type purified *E. canis* polypeptides comprise SEQ ID NO:2, 15, 16, 17, or combinations thereof.

* * * * *